US009375452B2

(12) United States Patent
Edge et al.

(10) Patent No.: US 9,375,452 B2
(45) Date of Patent: *Jun. 28, 2016

(54) USE OF STEM CELLS TO GENERATE INNER EAR CELLS

(71) Applicant: Massachusetts Eye and Ear Infirmary, Boston, MA (US)

(72) Inventors: Albert Edge, Brookline, MA (US); Stefan Heller, Menlo Park, CA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 51 days.

This patent is subject to a terminal disclaimer.

(21) Appl. No.: 14/208,284

(22) Filed: Mar. 13, 2014

(65) Prior Publication Data
US 2015/0030568 A1    Jan. 29, 2015

Related U.S. Application Data

(63) Continuation of application No. 10/989,649, filed on Nov. 15, 2004, now Pat. No. 8,673,634.

(60) Provisional application No. 60/519,712, filed on Nov. 13, 2003, provisional application No. 60/605,746, filed on Aug. 31, 2004.

(51) Int. Cl.
| *A61K 35/12* | (2015.01) |
| *A61K 35/30* | (2015.01) |
| *C12N 5/0793* | (2010.01) |
| *A61K 35/55* | (2015.01) |
| *A61K 38/17* | (2006.01) |
| *G01N 33/50* | (2006.01) |
| *A61K 9/00* | (2006.01) |

(52) U.S. Cl.
CPC .............. *A61K 35/30* (2013.01); *A61K 9/0046* (2013.01); *A61K 35/55* (2013.01); *A61K 38/1709* (2013.01); *C12N 5/062* (2013.01); *C12N 5/0619* (2013.01); *G01N 33/5073* (2013.01); *A61K 35/12* (2013.01); *C12N 2501/105* (2013.01); *C12N 2501/11* (2013.01); *C12N 2501/115* (2013.01); *C12N 2501/41* (2013.01); *C12N 2506/02* (2013.01)

(58) Field of Classification Search
CPC ..... A61K 38/00; A61K 38/195; A61K 35/12; A61K 35/55; A61K 38/1709; A61K 9/0046; A61K 35/30; C07K 14/522; C12N 5/062; C12N 2501/105; C12N 2501/11; C12N 5/0619; C12N 2501/41; C12N 2506/02; C12N 2501/115; G01N 33/5073
USPC ........................................................ 424/93.7
See application file for complete search history.

(56) References Cited

U.S. PATENT DOCUMENTS

| 6,277,820 | B1 | 8/2001 | Rosenthal et al. |
| 6,589,505 | B1 | 7/2003 | Roussel et al. |
| 6,929,948 | B1* | 8/2005 | Smith ................. C12N 5/0603 424/93.2 |
| 7,390,659 | B2 | 6/2008 | Jessell et al. |
| 7,604,992 | B2 | 10/2009 | Reubinoff |
| 8,617,810 | B2 | 12/2013 | Heller et al. |
| 8,673,634 | B2 | 3/2014 | Li et al. |
| 2002/0151056 | A1* | 10/2002 | Sasai ........................ C07K 6/18 435/368 |
| 2003/0114381 | A1* | 6/2003 | Cotanche ............. C12N 5/0623 424/93.7 |
| 2004/0166091 | A1 | 8/2004 | Brough |
| 2004/0231009 | A1 | 11/2004 | Zoghbi et al. |
| 2005/0019801 | A1 | 1/2005 | Rubin et al. |
| 2008/0267929 | A1 | 10/2008 | Li et al. |
| 2009/0004736 | A1 | 1/2009 | Reubinoff |

FOREIGN PATENT DOCUMENTS

| JP | 2003-093049 | | 4/2003 |
| JP | 2003093049 | * | 4/2003 |
| JP | 2006-117536 | | 5/2006 |
| WO | 01/98463 | | 12/2001 |
| WO | 03/104444 | | 10/2003 |
| WO | WO/03/104444 | * | 12/2003 |

OTHER PUBLICATIONS

Amit et al J. Anat. 200:225-232, 2002.*
Gorba et al Pharmacol Res, 47(4): 2003, 269-78.*
Koestenbauer et al Am J Reprod Immunol. 2006; 55(3):169-80.*
Fred Gage Nature 392: 18-24, 1998.*
Samstein et al Journal of American Society of Nephrology 12: 182-193, 2001.*
Sekiya et al Neurosurgery 52:900-907, 2003).*
Li et al (Proc Natl Acad Sci U S A. Nov. 11, 2003;100(23):13495-500.*
Li et al (Nature Medicine, 2003, 9, 1293-1299.*
"Scientific Considerations Related to Developing Follow-on Protein Products," pp. 1-12 (2004).
Aletsee et al., "The Disintegrin Kistrin Inhibits Neurite Extension from Spiral Ganglion Explants Cultured on Laminin," Audiol. Neurootol. 6:57-65 (2001).
Altschul et al., "Gapped BLAST and PSI-BLAST: A New Generation of Protein Database Search Programs," Nucl. Acids Res. 25:3389-3402 (1997).
Amit and Itskovitz-Eldor, "Derivation and Spontaneous Differentiation of Human Embryonic Stem Cells," J. Anat. 200:225-232 (2002).
Andrews et al., "Embryonic Stem (ES) Cells and Embryonal Carcinoma (EC) Cells: Opposite Sides of the Same Coin," Biochem Soc. Trans. 33:1526-1530 (2005).

(Continued)

*Primary Examiner* — Anoop Singh
(74) *Attorney, Agent, or Firm* — Fish & Richardson P.C.

(57) ABSTRACT

This invention relates generally to methods and compositions for inducing stem cell or progenitor cell differentiation, and more particularly to methods and compositions for inducing differentiation of stem cells and/or progenitor cells into cells that function within the inner ear.

5 Claims, 9 Drawing Sheets

(56) References Cited

OTHER PUBLICATIONS

Armstrong et al., "Porcine Neural Xenografts in the Immunocompetent Rat: Immune Response Following Grafting of Expanded Neural Precursor Cells," Neuroscience 106:201-216 (2001).
Aubert et al., "Functional Gene Screening in Embryonic Stem Cells Implicates Wnt Antagonism in Neural Differentiation," Nat. Biotechnol. 20:1240-1243 (2002).
Bain et al., "Embryonic Stem Cells Express Neuronal Properties in Vitro," Developmental Biol. 168:342-357 (1995).
Barker et al., "A Role of Complement in the Rejection of Porcine Ventral Mesencephalic Xenografts in a Rat Model of Parkinson's Disease," J. Neurosci. 20:3415-3424 (2000).
Bermingham et al., "Math1 : An Essential Gene for the Generation of Inner Ear Hair Cells," Science 284:1837-1841 (1999).
Bowie et al., "Deciphering the Message in Protein Sequences: Tolerance to Amino Acid Substitutions," Science 247:1306-1310 (1990).
Brigande et al., "Quo vadis, hair cell regeneration?" Nature Neurosci. 12(6): 679-685 (2009).
Brors et al., "EphA4 Provides Repulsive Signals to Developing Cochlear Ganglion Neurites Mediated through Ephrin-B2 and -B3," J. Comp. Neurol. 462:90-100 (2003).
Buehr et al., "Genesis of Embryonic Stem Cells," Philos. Trans. R. Soc. Lond. B. Biol. Sci. 358:1397-1402 (2003).
Cacciabue-Rivolta et al., "Retinoic Acid Promotes Hair Cell Differentiation in an Inner Ear Epithelial Cell Line," Association for Research in Otolaryngology, Volume and Issue No. 25, Midwinter Meeting, St. Petersburg Beach, FL Abstract No. 290, Jan. 28, 2002.
Charron et al., "The Morphogen Sonic Hedgehog is an Axonal Chemo attractant that Collaborates with Netrin-1 in Midline Axon Guidance," Cell 113:1 1-23 (2003).
Coppola et al., "Dissection of NT3 functions in vivo by gene replacement strategy," Development 128: 4315-4327, 2001.
Corrales et al., "Engraftment and Differentiation of Embryonic Stem Cell-Derived Neural Progenitor Cells in the Cochlear Nerve Trunk: Growth of Processes into the Organ of Corti," J. Neurobiol. 66:1489-1500 (2006).
Cosgrove et al., "Integrin α1/31 and Transforming Growth Factor-/31 Play Distinct Roles in Alport Glomerular Pathogenesis and Serve as Dual Targets for Metabolic Therapy," Am. J. Pathol. 157:1649-1659 (2000).
Cowan et al., "Derivation of Embryonic Stem-Cell Lines from Human Blastocysts," N. Engl. J. Med. 350: 1353-1356, 2004.
Dazert et al., "Regeneration of Inner Ear Cells from Stem Cell Precursors—A Future Concept for Hearing Rehabilitation?" DNA Cell Biol. 22:565-570 (2003).
Fitzgerald et al., "Clinical Neuroanatomy and Related Neuroscience," Table of Contents, Saunders publishing, Fourth ed. (2001).
Fujino et al., "Transplantation of neural stem cells into explants of rat inner ear," Acta Otolaryngol. Suppl. 551:31-33 (2004).
Gage, "Cell Therapy," Nature, 392:18-24 (1998).
GenBank Accession No. AY422195, "*Homo sapiens* sonic hedgehog homolog (Drosophila) (SHH) gene, complete eds," Oct. 14, 2003.
GenBank Accession No. NM_021044, "*Homo sapiens* desert hedgehog homolog (Drosophila) (DHH), mRNA," Oct. 5, 2003.
GenBank Accession No. XM_050846, "*Homo sapiens* Indian hedgehog homolog (Drosophila) (IHH), mRNA," Oct. 17, 2003.
Gillespie et al., "LIF is more potent than BDNF in promoting neurite outgrowth of mammalian auditory neurons in vitro," NeuroReport 12:275-279 (2001).
Ginis et al., "Differences between Human and Mouse Embryonic Stem Cells," Dev. Biol. 269:360-380 (2004).
Gorba et al., "Pharmacological Potential of Embryonic Stem Cells," Pharmacol. Res. 47:269-278 (2003).
Groves et al., "Competence, Specification and Commitment in Otic Placode Induction," Development 127:3489-3499 (2000).

Hadjantonakis et al., "Generating Green Florescent Mice by Gennline Transmission of Green Fluorescent ES Cells," Mech. Dev. 76:79-90 (1998).
Hamburger et al., "A Series of Nonnal Stages in the Development of the Chick Embryo," J. Morphol. 88:49-92 (1951).
Hilbert and Ferrans, "Porcine Aortic Valve Bioprostheses: Morphologic and Functional Considerations," J. Long Term Eff. Med. Implants. 2:99-112 (1992).
Hildebrand et al., "Advances in Molecular and Cellular Therapies for Hearing Loss," American Soc. Gene Ther. 16(2):224-236 (2008).
Howard et al., "Eph Receptor Deficiencies Lead to Altered Cochlear Function," Hearing Res. 178:1 18-130 (2003).
Ito et al., "Survival of Neural Stem Cells in the Cochlea," Acta Otolaryngol. 121:140-142 (2001).
Kawamoto et al., "Math 1 Gene Transfer Generates New Cochlear Hair Cells in Mature Guinea Pigs In Vivo," J. Neurosci. 23:4395-4400 (2003).
Kehat et al., "Human Embryonic System Cells Can Differentiate into Myocytes with Structural and Functional Properties of Cardiomyocytes," J. Clin. Invest. 108:407-414 (2001).
Koestenbauer et al., "Embryonic Stem Cells: Similarities and Differences Between Human and Murine Embryonic Stem Cells," Am. J. Reprod. Immunol 55:169-180 (2006).
Lanford et al., "Notch Signaling Pathway Mediates Hair Cell Development in Mammalian Cochlea," Nat. Genet. 21:289-292 (1999).
Lee et al., "Autoproteolysis in Hedgehog Protein Biogenesis," Science 266: 1528-1537 (1994).
Lee et al., "Efficient Generation of Midbrain and Hindbrain Neurons from Mouse Embryonic Stem Cells," Nat. Biotech. 18:675-679 (2000).
Li et al., "Pluripotent Stem Cells from the Adult Mouse Inner Ear," Nature Medicine 9:1293-1299 (2003).
Li et al., "Differentiation of neurons from neural precursors generated in floating spheres from embryonic stem cells," BMC Neurosci. 10:122 (Sep. 24, 2009).
Li et al., "Generation of Hair Cells by Stepwise Differentiation of Embryonic Stem Cells," Proc. Natl. Acad. Sci. U.S.A. 100:13495-13500 (2003).
Loseva et al., "Comparison of Relative Processes in the Rat Brain Elicited by Xenotransplantation of Nervous Tissues of Chicken or Pulmonate Snail," Brain Res., 915:125-132 (2001).
Mangi et al., "Mesenchymal Stem Cells Modified with Akt Prevent Remodeling and Restore Performance of Infarcted Hearts," Nat. Med., 9:1195-1201 (2003).
Matsui et al., "Regeneration and Replacement in the Vertebrate Inner Ear," Drug Discov Today 10:1307-1312 (2005).
Matsuoka et al., "In Vivo and In Vitro Characterization of Bone Marrow-Derived Stem Cells in the Cochlea," Laryngoscope 1 16:1363-1367 (2006).
Morrison et al., "Expression of Deltal and Serratel (Jagged1) in the Mouse Inner Ear," Mech. Dev. 84:169-172 (1999).
Morsli et al., "Development of the Mouse Inner Ear and Origin of Its Sensory Organs," J. Neurosci. 18:3327-3335 (1998).
Nagy et al., "Derivation of Completely Cell Culture-Derived Mice from Early-Passage Embryonic Stems Cells," Proc. Natl. Acad. Sci. U.S.A. 90:8424-8428 (1993).
Okabe et al., "Development of Neuronal Precursor Cells and Functional Postmitotic Neurons from Embryonic Stem Cells in Vitro," Mechanisms of Development 59:89-102 (1996).
Pedersen, "Embryonic Stem Cells for Medicine," Scientific American 69-73 (1999).
Pera et al., J. Cell Science 113:5-10 (2000).
Petit, Christine, "Usher Syndrome: From Genetics to Pathogenesis," Annu. Rev. Genomics Hum. Genetics 2:271-297 (2001).
Pfeifer and Verma, "Gene Therapy: Promises and Problems," Ann. Rev. Genomics Hum. Genetics 2:177-211 (2001).
Pirity et al., "Embryonic Stem Cells, Creating Transgenic Animals," Methods Cell Biol. 57:279-293 (1998).
Plum et al., "Connexin3 1-Deficiency in Mice Causes Transient Placental Dysmorphogenesis but does not impair hearing and skin differentiation," Dev. Biol. 231:334-347 (2001).

(56) References Cited

OTHER PUBLICATIONS

Porter et al., "The Product of Hedgehog Autoproteolytic Cleavage Active in Local and Long-Range Signaling," Nature 374:363-366 (1995).
Reubinoff et al., "Embryonic stem cell lines from human blastocysts: somatic differentiation in vitro," Nature BioTechnology 18:399-404, 2000.
Reubinoff et al., "Neural progenitors from human embryonic stem cells," Nature Biotechnology 19:1134-1140 (2001).
Rivolta et al., "Generation of Inner Ear cell Types from Embryonic Stem Cells," in Embryonic Stem Cell Protocols, vol. 2: Differentiation Models, second edition Turksen, Ed. (Humana Press, Totowa, NJ 2006).
Sakamoto et al., "Fates of Mouse Embryonic Stem Cells Transplanted into the Inner Ears of Adult Mice and Embryonic Chickens," Acta Otolarynol. Supp. 551:48-52 (2004).
Samstein et al., "Physiologic and Immunologic Hurdles to Xenotransplantation," J. Am. Soc. Nephrol. 12:182-193 (2001).
Schuldiner et al, "Effects of eight growth factors on the differentiation of cells derived from human embryonic stem cells," Proc. Natl. Acad. Sci. U.S.A. 97: 11307-11312, 2000.
Sekiya et al., Neurosurgery 52:900-907 (2003).
Shi et al., "BMP4 induction of sensory neurons from human embryonic stem cells and reinnervation of sensory epithelium," Eur. J. Neuro. 26:3016-3023 (2007).
Skolnik et al., "From Genes to Protein Structure and Function: Novel Applications of Computational Approaches in the Genomic Era," Trends Biotechnol. 18:34-39 (2000).
Srour et al., "Ex Vivo Expansion of Hematopoietic Stem and Progenitor Cells: Are we there yet?" J. Hematother. 8:93-102 (1999).
Sumitran et al., "Porcine Embryonic Brain Cell Cytotoxicity Mediated by Human Natural Killer Cells," Cell Transplant. 8:601-610 (1999).
Takahashi et al., "Widespread Integration and Survival of Adult-Derived Neural Progenitor Cells in the Developin.e; Optic Retina," Mol. Cell. Neurosci, 12:340-348 (1998).
Tateya et al., "Fate of Neural Stem Cells Grafted into Injured Inner Ears of Mice," Neuroreport. 14:1677-81 (2003).
Tessaeollo et al., "NT-3 Replacement with Brain-derived Neurotrophic Factor Redirects Vestibular Nerve Fibers to the Cochlea," J. Neurosci. 24:2575-2584 (2004).
Tessarollo et al., "NT-3 Replacement with Brain-Derived Neurotrophic Factor Redirects Vestibular Nerve Fibers to the Chochlea," J. Neuroscience 24:2575-2584 (2004).
Van Asperen et al., "Risk of Otitis Extema After Swimming in Recreational Fresh Water with Pseudomonas Aeurginosa," Brit. Med. J. 311:1407-1410 (1995).
Vats et al., "Stem Cells: Sources and Applications," Clin. Otolaryngol. 27:227-232 (2002).
Verma and Somia, "Gene Therapy: Promises, Problems and Prospects," Nature 389:239-242 (1997).
Woods et al., "Math1 regulates development of the sensory epithelium in the mammalian cochlea," Nature Neuroscience 7(12):1310-1318 (2004).
Yamamoto et al., "Inhibition of Notch/RBP-J signaling induces hair cell formation in neonate mouse cochleas," J. Mol. Med. 84(1):37-45 (2006).
Zhang et al., "In vitro differentiation of transplantable neural precursors from human embryonic stem cells," Nature Biotechnology, 19:1129-1133 (2001).
Zheng et al., "Overexpression of Math1 Induces Robust Production of Extra Hair Cells in Postnatal Rat Inner Ears," Nat. Neurosci., 3:580-586 (2000).
Zheng et al., "The Role of Six 1 in Mammalian Auditory System Development," Development 130:3989-4000 (2003).
Zinc et al., "Notch signaling regulates the pattern of auditory hair cell differentiation in mammals," Development 127:3373-3383 (2000).
Zinc et al., "Notch/Notch ligands and Math1 expression patterns in the organ of Corti of wild-type and Hes1 and Hes5 mutant mice," Hearing Research 170:22-31 (2002).
International Preliminary Report on Patentability received in PCT/US05/30714 mailed Apr. 1, 2008.
International Search Report received in PCT/US05/30714 mailed Mar. 4, 2008.
Lanford et al., "Expression of Math1 and HES5 in the cochleae of wildtype and Jag2 mutant mice," J. Assoc. Res. Otolaryngol. 1(2):161-171 (2000).
Li et al., Current Biology 8:971-974 (1998).
Smith, "Culture and Differentiation of embryonic stem cells," J. Tissue Cult. Methods 13:89-94, 1991.
Written Opinion of the International Searching Authority received in PCT/US05/30714 mailed Mar. 4, 2008.
Jeon et al., "Bone Marrow Mesenchymal Stem Cells are Progenitors In Vitro for Inner Ear Hair Cells," Mol. Cell Neurosci., 34(1):59-68 (Jan. 2007) *Author Manuscript*.
Kitchens et al., "FGF and EGF are mitogens for immortalized neural progenitors," J. Neurobiol., 25(7):797-807 (1994) *Abstract Only*.
Zhang, "Neural subtype specification from embryonic stem cells," Brain Pathol. 16:132-142 (2006) *Abstract Only*.

\* cited by examiner

SHH Amino Acid Sequence (GenBank: AY422195)

MLLLARCLLLVLVSSLLVCSGLACGPGRGFGKRRHPKKLTPLAYKQFIPNVAEKTLGAG
RYEGKISRNSERFKELTPNYNPDIIFKDEENTGADRLMTQRCKDKLNALAISVMNQWPG
VKLRVTEGWDEDGHHSEESLHYEGRAVDITTSDRDRSKYGMLARLAVEAGFDWVYYESK
AHIHCSVKAENSVAAKSGGCFPGSATVHLEQGGTKLVKDLSPGDRVLAADDQGRLLYSD
FLTFLDRDDGAKKVFYVIETREPRERLLLTAAHLLFVAPHNDSATGEPEASSGSGPPSG
GALGPRALFASRVRPGQRVYVVAERDGDRRLLPAAVHSVTLSEEAAGAYAPLTAQGTIL
INRVLASCYAVIEEHSWAHRAFAPFRLAHALLAALAPARTDRGGDSGGGDRGGGGGRVA
LTAPGAADAPGAGATAGIHWYSQLLYQIGTWLLDSEALHPLGMAVKSS

FIG. 1

Shh Protein coding Sequence (GenBank: AY422195)

atgctgctgc tggcgagatg tctgctgcta gtcctcgtct cctcgctgct
ggtatgctcg ggactggcgt gcggaccggg caggggggttc gggaagagga
ggcaccccaa aaagctgacc cctttagcct acaagcagtt tatccccaat
gtggccgaga agaccctagg cgccagcgga aggtatgaag gaagatctc
cagaaactcc gagcgattta aggaactcac cccaattac aaccccgaca
tcatatttaa ggatgaagaa aacaccggag cggacaggct gatgactcag
aggtgtaagg acaagttgaa cgctttggcc atctcggtga tgaaccagtg
gccaggagtg aaactgcggg tgaccgaggg ctgggacgaa gatggccacc
actcagagga gtctctgcac tacgagggcc gcgcagtgga catcaccacg
tctgaccgcg accgcagcaa gtacggcatg ctggccgcc tggcggtgga
ggccggcttc gactgggtgt actacgagtc caaggcacat atccactgct
cggtgaaagc agagaactcg gtggcggcca aatcgggagg ctgcttcccg
ggctcggcca cggtgcacct ggagcagggc ggcaccaagc tggtgaagga
cctgagcccc ggggaccgcg tgctggcggc ggacgaccag ggccggctgc
tctacagcga cttcctcact ttcctggacc gcgacgacgg cgccaagaag
gtcttctacg tgatcgagac gcgggagccg cgcgagcgcc tgctgctcac
cgccgcgcac ctgctctttg tggccgcca caacgactcg ccaccggggg
agcccgaggc gtcctcgggc tcggggccgc cttccggggg cgcactgggg
cctcgggcgc tgttcgccag ccgcgtgcgc ccgggccagc gcgtgtacgt
ggtggccgag cgtgacgggg accgccggct cctgcccgcc gctgtgcaca
gcgtgaccct aagcgaggag gccgcgggcg cctacgcgcc gctcacggcc
cagggcacca ttctcatcaa ccgggtgctg gcctcgtgct acgcggtcat
cgaggagcac agctgggcgc accgggcctt cgcgcccttc cgcctggcgc
acgcgctcct ggctgcactg gcgcccgcgc acggaccg cggcggggac
agcggcggcg gggaccgcgg gggcggcggc ggcagagtag ccctaaccgc
tccaggtgct gccgacgctc cgggtgcggg ggccaccgcg ggcatccact
ggtactcgca gctgctctac caaataggca cctggctcct ggacagcgag
gccctgcacc cgctgggcat ggcggtcaag tccagctga

FIG. 2

Indian Hedgehog Amino acid sequence (GenBank XM_050846)

MSPARLRPRLHFCLVLLLLLVVPAAWGCPGRVVGSRRRPPRKLVPLAYKQFSPNVPEK
TLGASGRYEGKIARSSERFKELTPNYNPDIIFKDEENTGADRLMTQRCKDRLNSLAISV
MNQWPGVKLRVTEGWDEDGHHSEESLHYEGRAVDITTSDRDRNKYGLLARLAVEAGFDW
VYYESKAHVHCSVKSEHSAAAKTGGCFPAGAQVRLESGARVALSAVRPGDRVLAMGEDG
SPTFSDVLIFLDREPHRLRAFQVIETQDPPRRLALTPAHLLFTADNHTEPAARFRATFA
SHVQPGQYVLVAGVPGLQPARVAAVSTHVALGAYAPLTKHGTLVVEDVVASCFAAVADH
HLAQLAFWPLRLFHSLAWGSWTPGEGVHWYPQLLYRLGRLLEEGSFHPLGMSGAGS

FIG. 3

Desert Hedgehog Amino acid sequence (GenBank NM_021044)

MALLTNLLPLCCLALLALPAQSCGPGRGPVGRRRYARKQLVPLLYKQFVPGVPERTLGASGPAEG
RVARGSERFRDLVPNYNPDIHFKDEENSGADRLMTERCKERVNALAIAVMNMWPGVRLRVTEGW
DEDGHHAQDSLHYEGRALDITTSDRDRNKYGLLARLAVEAGFDWVYYESRNHVHVSVKADNSL
AVRAGGCFPGNATVRLWSGERKGLRELHRGDWVLAADASGRVVPTPVLLFLDRDLQRRASFVA
VETEWPPRKLLLTPWHLVFAARGPAPAPGDFAPVFARRLRAGDSVLAPGGDALRPARVARVARE
EAVGVFAPLTAHGTLLVNDVLASCYAVLESHQWAHRAFAPLRLLHALGALLPGGAVQPTGMHW
YSRLLYRLAEELLG

FIG. 4

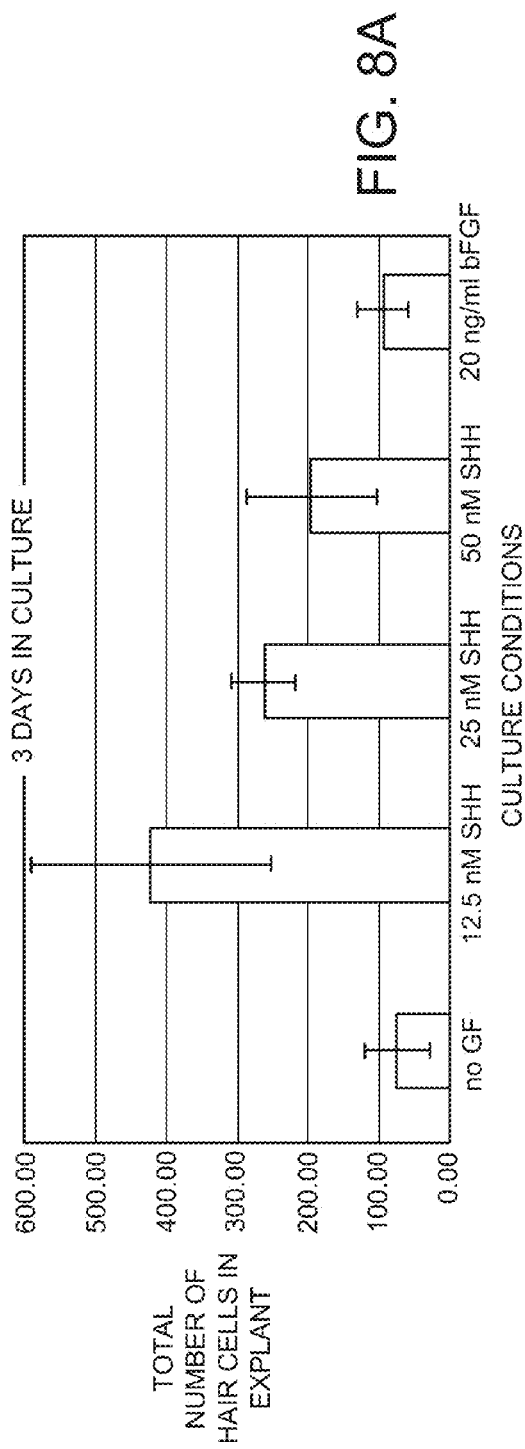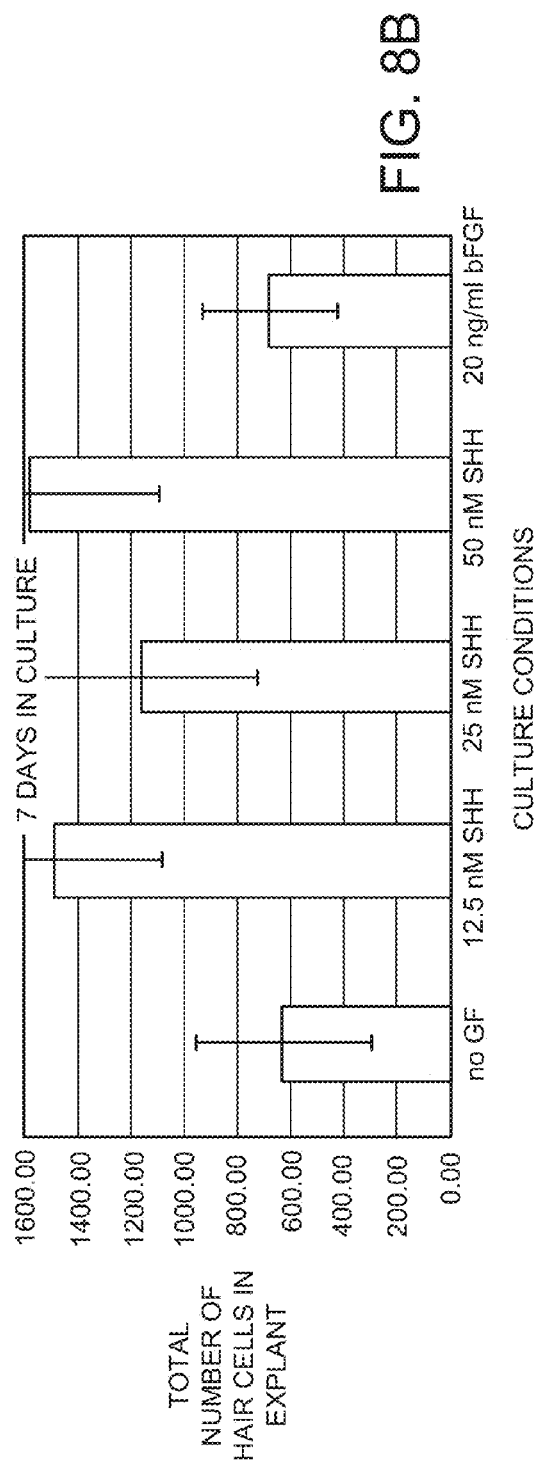

USE OF STEM CELLS TO GENERATE INNER EAR CELLS

This application is a continuation of U.S. Ser. No. 10/989,649, filed Nov. 15, 2004, which claims the benefit of the filing date of U.S. Ser. No. 60/605,746, which was filed on Aug. 31, 2004. The contents of the prior provisional applications are hereby incorporated in the present application in their entirety.

TECHNICAL FIELD

This invention generally relates to compositions and methods for inducing cellular differentiation (e.g., complete or partial differentiation of stem cells into cells capable of functioning as sensory cells of the ear) and to assays and methods of treatment that employ the stem cells or the more fully differentiated cells into which they develop.

BACKGROUND

More than 5% of the people in industrialized nations have significant hearing problems that range in severity from modest difficulty with speech comprehension to profound deafness. Hearing loss is age-related, as about 4% of people under 45 years old and about 34% of those over 65 years old have debilitating hearing loss. In most cases, the cause is related to degeneration and death of hair cells and their associated spiral ganglion neurons.

The ear is composed of four main sections: the external ear, middle ear, inner ear, and the transmission pathway to the hearing center in the brain. The inner ear is a capsule of very dense bone containing a fluid that communicates with the middle ear. Small bones within the middle ear (the malleus, incus, and stapes) transmit sound energy from the tympanic membrane to the oval window at the entrance to the cochlea of the inner ear. The action of the stapes at the oval window exerts pressure on the fluid within the cochlea. The pressure is transmitted through the cochlea, ultimately causing a second window, the round window to oscillate. A basilar membrane that defines the fluid-filled chambers of the cochlea then transmits the oscillations to the organ of Corti, which contains about 13,000 mechanosensory cells called hair cells. Hair cells are located in the epithelial lining of the inner ear (in the cochlear organ of Corti, as mentioned), as well as in the vestibular sensory epithelia of the saccular macula, the utricular macula, and the cristae of the three semicircular canals of the labyrinth. The cochlear hair cells send signals to the cochlear spiral ganglion, and the clustered neuronal cell bodies convey those signals to the cochlear nucleus of the brain stem (see FIGS. 5A, 5B, and 5C).

SUMMARY

The present invention features compositions and methods related to stem cells and cells of the inner ear. The methods include those for producing (e.g., isolating or obtaining) stem cells or progenitor cells from a tissue (e.g., a tissue within the inner ear) and for identifying agents that mediate complete or partial differentiation of those cells to or toward a mature cell type of the inner ear (e.g., a hair cell or spiral ganglion neuron). We may refer to these agents as "differentiation" agents or compounds. Other methods provide treatment for patients who have, or who are at risk for developing, an auditory disorder. The methods of treatment include steps whereby one administers a differentiation agent (e.g., an agent identified by a screening method described herein), a stem cell or progenitor cell (e.g., a cell isolated by the methods described herein), or both (i.e., both a differentiation agent and a stem cell and/or progenitor cell) to the inner ear of the patient. The compositions include stem cells and progenitor cells isolated by the methods described herein as well as pharmaceutical compositions and kits containing them. The methods of the invention can be practiced using either stem cells or cells that are partially differentiated (progenitor cells).

In one aspect, the invention features screening methods for identifying agents that can increase or decrease the expression of one or more auditory proteins within a cell (regardless of the extent to which that cell has differentiated). The change in expression can be, but is not necessarily, a robust change. For example, a candidate agent may increase the expression of an auditory protein from an essentially undetectable level to a readily detectable level. It may also increase expression to a certain degree (e.g., there may be about a 1-, 2-, or 5-fold increase in expression). The protein analyzed (i.e., the auditory protein) can be any protein that is ordinarily expressed in a mature cell of the inner ear (e.g., a hair cell or spiral ganglion cell of an adult who has normal hearing), but expression is not necessarily specific for an inner ear cell. For example, the protein can be one that is expressed in other cell types, and it may be expressed at varying levels as a stem cell differentiates into a progenitor cell and finally into a completely differentiated cell. Proteins that are expressed in inner ear cells (e.g., in hair cells and spiral ganglion cells) are well known in the art.

The screening methods include providing a cell or a population of cells, which may contain a single cell type or a variety of cell types, including cells that may be undifferentiated (i.e., pluripotent stem cells) less than fully differentiated (i.e., progenitor cells) or fully differentiated (e.g., recognizable as hair cells or spiral ganglion cells). Where a population of test cells is used, the proportion of stem cells within the test population can vary. For example, the population can contain few stem cells (e.g., about 1-10%) a moderate proportion of stem cells (e.g., about 10-90% (e.g., about 20, 25, 30, 40, 50, 60, 70, 75, 80, or 85% stem cells)) or many stem cells (e.g., at least 90% of the population (e.g., 92, 94, 96, 97, 98, or 99%) can be stem cells). The cells will have the potential to differentiate into a completely or partially differentiated cell of the inner ear (e.g., the cell can be a pluripotent stem cell that differentiates into a cell that expresses one or more auditory proteins). Partially differentiated cells are useful in the treatment methods (whether therapeutic or prophylactic) so long as they express a sufficient number and type of auditory-specific proteins to confer a benefit on the patient (e.g., improved hearing).

With respect to their source, the cells employed in the screening or treatment methods can be obtained from a mammal, such as a human, from any developmental stage. For example, the cells can be derived from an embryo, fetus or post-natal mammal (e.g., an infant, child, adolescent, or adult (e.g., an adult human)). More specifically, the stem cell or the progenitor cell can be obtained from the cochlear organ of Corti, the modiolus (center) of the cochlea, the spiral ganglion of the cochlea, the vestibular sensory epithelia of the saccular macula, the utricular macula, or the cristae of the semicircular canals (see FIGS. 5A, 5B, and 5C). The stem cell or progenitor cell can also be obtained, however, from other tissues such as bone marrow, blood, skin, or an eye. The cells employed can be obtained from a single source (e.g., the ear or a structure or tissue within the ear) or a combination of sources (e.g., the ear and one or more peripheral tissues (e.g., bone marrow, blood, skin, or an eye)). The cells can also be obtained from a patient to whom they will subsequently be readministered.

Where the methods are carried out in cell culture, one can use an essentially pure population of cells (e.g., an essentially pure population of stem cells (e.g., a population in which about 90% or more of the cells are stem cells). Individual cells (e.g., a single cell placed within the well of a tissue culture plate) can also be analyzed (by, for example, an amplification technique such as "single-cell" PCR). Once the cell or cell population is selected, the cell(s) can be contacted with a candidate agent or exposed to certain environmental conditions (e.g., conditions that vary from physiologic conditions (e.g., increased or decreased temperature, abnormal levels of $CO_2$ or other gases (e.g., oxygen), or non-physiological pH)). Following exposure to the candidate agent or environmental change, one can determine whether the level of expression of an auditory protein is more (or less) than the level prior to exposure to the agent (or relative to a reference standard). More than one auditory protein can be assessed, at the same time or sequentially. To assess expression, one can examine protein levels per se or the level of RNA transcription. Numerous methods are known in the art that can be suitably employed to assess either protein or RNA expression. An increase in expression of the auditory protein indicates that the agent can promote the expression of the auditory protein within the cell, thereby promoting at least partial differentiation of a cell (e.g., a stem cell) into a more mature cell of the inner ear. The ultimate goal of the screening methods is to identify an agent or group of agents or conditions that increase the expression of auditory proteins that mediate the sense of hearing and can, therefore, be used to generate cells that improve a patient's ability to hear or maintain their balance. No particular mechanism of action is required or implied. The agent(s) and/or condition(s) may act directly or indirectly on the transcriptional machinery for the auditory protein in question.

The candidate agents can be essentially any nucleic acid (e.g., a gene or gene fragment that encodes a polypeptide (e.g., a functional protein) such as a growth factor or other cytokine (e.g., an interleukin)), any polypeptide per se (which may be a full-length protein or a biologically active fragment or other mutant thereof), or any small molecule. The small molecules can include those contained with commercially available compound libraries (suppliers include ChemBridge Corp (San Diego, Calif.) and ChemDiv (San Diego, Calif.)). The screening assays can be configured as "high throughput" assays to screen many such agents at once. For example, the agents and/or cells to be assessed can be presented in an array. More specifically, the candidate agent can be, for example, a nucleic acid that encodes, or a polypeptide that is, a polypeptide active in the cellular biochemical pathway of which Notch, WNT, or Sonic hedgehog are a part (e.g., WNT1, WNT10B, WNT11, WNT13, WNT14, WNT15, WNT2, WNT2B, WNT5a, WNT7a, or WNT8B); a homolog of Notch, WNT, or Sonic hedgehog; or a biologically active fragment or other variant of Notch, WNT, or Sonic hedgehog. For example, the nucleic acid can encode a fragment of Sonic hedgehog, such as SHH-N or a variant thereof (e.g., an SHH-N fragment that contains a limited number (e.g., 1-10) of conservative amino acid substitutions), or a homolog of Sonic hedgehog, such as Indian hedgehog or Desert hedgehog or fragments or other mutants thereof (e.g., a fragment of Indian hedgehog or Desert hedgehog that corresponds to SHH-N). A homolog is a nucleic acid or polypeptide that is substantially identical to, for example, a Notch, WNT, or Sonic hedgehog nucleic acid or polypeptide and, preferably, functions in the pathways in which Notch, WNT, and Sonic hedgehog are active. Notch, WNT, or Sonic hedgehog from different species may also be described as homologs (e.g., a human sequence may be described as the homolog of a Notch protein from *Drosophila* or mouse). A first nucleic acid (whether genomic DNA, cDNA, RNA or a nucleic acid containing non-naturally occurring nucleotides) or polypeptide is substantially identical to a second nucleic acid or polypeptide, respectively, when the two are exhibit sequence similarity and at least one shared activity. Nucleic acids and polypeptides useful in the screening and therapeutic methods of the present invention can be substantially identical to a human Sonic hedgehog cDNA (SEQ ID NO:2; FIG. 2) or amino acid sequence (SEQ ID NO:8; FIG. 1). For example, a nucleic acid sequence substantially identical to human Sonic hedgehog cDNA is at least 80% identical (e.g., 85%, 90%, 95%, 98%, or 99%) to SEQ ID NO:2, and a substantially identical amino acid sequence is at least 80% identical (e.g., 85%, 90%, 95%, 98%, or 99%) to SEQ ID NO:1.

In particular embodiments, the nucleic acid can encode, or the polypeptide can be: Math1, parvalbumin 3, Brn3.1, Brn3.2, Hes1, Hes5, neurogenin-1, NeuroD, Jagged1, Jagged2, Delta1, Notch1, Lunatic fringe, Numb, Wnt7a, p27Kip1, Shh, Bmp4, Fgfr3, Fgfr1, Fgfr2, Fgf10, Fgf2, Fgf3, GATA3, Pax2, neurotrophin-3, BDNF, or a fragment or other mutant thereof (e.g., a fragment or other mutant that retains sufficient biological activity to function in a screening method or therapeutic method described herein).

Rather than, or in addition to, assessing the expression of one or more auditory proteins, the screening methods can be carried out by assessing a reporter gene that has been placed under the control of a sequence that regulates the expression of an auditory protein (e.g., a promoter and/or enhancer that directs expression of an auditory protein in vivo). Accordingly, in another aspect, the invention features methods of identifying differentiation agents that promote the expression of an auditory protein within a cell by providing a cell (any of the cells or populations of cells described above would be appropriate) containing a reporter gene operably linked to a promoter or promoter element (e.g., an enhancer region) of an auditory protein gene. As with the screening method described above, the cell(s) can be contacted with the candidate agent in vivo or in cell culture, and the level of expression of the reporter gene within the cell can be assessed. An increase in expression following exposure to the candidate agent indicates that the agent promotes the expression of the auditory protein within the cell. A decrease in reporter gene expression identifies the agent as a candidate inhibitor of auditory protein expression (proteins that inhibit the expression of an auditory protein are potential targets for inhibition; by inhibiting a protein that inhibits the expression of an auditory protein, one can promote expression of the auditory protein). Cells (e.g., stem cells, progenitor cells, or differentiated cells from the inner ear or another tissue) that contain the reporter constructs described herein (e.g., a plasmid bearing an auditory protein regulatory region operably linked to a reporter gene) are also within the scope of the present invention, as are the reporter constructs per se (e.g., the invention features nucleic acids, which may be further contained within a vector such as a plasmid, in which a regulatory region of an auditory protein (e.g., a Math1 regulatory region of a sonic hedgehog regulatory region) is operably linked to a reporter gene). The reporter gene can encode any detectable polypeptide. For example, the reporter gene can be a gene that encodes a fluorescent protein, an enzymatically active protein (e.g., β-galactosidase and chloramphenicol acetyltransferase), or a protein detectable in an antibody-based assay.

Other markers are known in the art and additional exemplary markers are described further below.

The screening methods described herein can be performed on a cell in cell culture under ex vivo conditions of pH and temperature suitable to maintain viability (such conditions are generally known in the art and exemplary conditions are provided below). Cells can also be treated in cell culture prior to administration to a patient.

The invention also features methods of isolating a stem cell or progenitor cell from the inner ear of an animal (e.g., a mammal such as a human, non-human primate, or other mammal such as a pig, cow, sheep, goat, horse, dog, cat, or rodent). These methods include providing tissue from the inner ear (e.g., a piece of tissue that includes hair cells or the membrane with which they are associated, or spiral ganglion cells). For example, the tissue can include at least a portion of the utricular maculae. The tissue can be disrupted by exposure to a chemical or mechanical force (or both). For example, the tissue can be exposed to a tissue-digesting enzyme, such as trypsin, and/or to a mechanical (e.g., physical) force such as trituration to break the tissue into smaller pieces. The treated tissue (e.g., enzyme-treated tissue (e.g., the enzyme-treated utricular maculae)) can optionally be soaked in fetal calf serum or other protein solution to neutralize or exhaust the enzyme (fully or partially); washed; and the disrupted tissue can be passed through a device such as a cell strainer that separates the stem cells or progenitor cells within the disrupted tissue from differentiated cells or cellular debris. The cells obtained may constitute an enriched population of stem cells and/or progenitor cells; isolation from all (or essentially all) differentiated cells or other cellular material within the tissue may be achieved but is not required to meet the definition of "isolated." Absolute purity is not required. The invention encompasses cells obtained by the isolation procedures described herein. The cells may be mixed with a cryoprotectant and stored or packaged into kits. Once obtained, the stem cells and/or progenitor cells can be expanded in culture.

Methods for treating patients (e.g., humans) who have, or who are at risk for developing, an auditory disorder, are also described and are within the scope of the present invention. These methods include administering a cell or population of cells (as described above; e.g. a stem cell and/or progenitor cell obtained from a tissue such as the ear) to the ear of the patient. The administered cells may be obtained by the methods described herein, and the starting material may be tissue obtained from the patient to be treated. In other embodiments, the methods include the step of administering a therapeutic agent that promotes the expression of an auditory protein within a cell within the inner ear (e.g., a differentiation agent as described herein or as identified by the screening methods described herein). When used, the differentiation agent can be administered to cells in culture or can be administered to the patient either alone (to stimulate the differentiation of stem cells or progenitor cells within the patient's inner ear) or together with undifferentiated cells (e.g., undifferentiated cells isolated by the methods described herein). The differentiation agent can be, for example, an agonist of the hedgehog pathway, such as an agonist of Sonic hedgehog (e.g., Hh-Ag1.3).

As noted, the invention also features a stem cell or progenitor cell (either of which may cluster into cellular spheres) isolated by the methods described herein, compositions containing them, and kits that include them (with, for example, instructions for inducing differentiation; for expanding the cells in culture; and/or for administering the cells to a patient or to a cell (e.g., a cell in culture) to promote its differentiation). The instructions can be printed or in another form (e.g., provided on audio- or videotape).

There may be certain advantages to the use of stem cells and/or progenitor cells for the treatment of hearing disorders. For example, stem cells are readily expandable and can be expanded to generate a desired tissue or cell type (e.g., hair cells or spiral ganglion cells) for application to a patient. The stem cells can be obtained from humans for clinical applications. Because the stem cells can be harvested from a human, and in particular can be harvested from the human in need of treatment, the immunological hurdles common in xeno- and allotransplantation experiments can be largely avoided.

Other features and advantages of the invention will be apparent from the accompanying description and the claims. The contents of all references, pending patent applications and published patents, cited throughout this application are hereby expressly incorporated by reference. In case of conflict, the present specification, including definitions, will control.

BRIEF DESCRIPTION OF THE DRAWINGS

FIG. 1 is the amino acid sequence of an SHH polypeptide from human (GenBank Accession No. AY422195; SEQ ID NO:1). The amino acids of the SHH-N polypeptide are underlined.

FIG. 2 is a protein-coding nucleic acid sequence of SHH from human (GenBank Accession No. AY422195; SEQ ID NO:2).

FIG. 3 is the amino acid sequence of an Indian hedgehog (Ihh) polypeptide from human (GenBank Accession No. XM_050846; SEQ ID NO:3).

FIG. 4 is the amino acid sequence of a Desert hedgehog (Dhh) polypeptide from human (GenBank Accession No. NM_021044; SEQ ID NO:4).

FIG. 8A is a graph illustrating a quantitative analysis of the promoting effect of SHH on the number of hair cells generated in otic vesicles after 3 days in culture. The basic serum-free culture conditions ("no GF") include serum-free knock-out DMEM medium with N2 supplement.

FIG. 8B is a graph illustrating a quantitative analysis of the promoting effect of SHH on the number of hair cells generated in otic vesicles after seven days in culture. Serum conditions are as described in FIG. 8A.

DETAILED DESCRIPTION

Figure 5A:
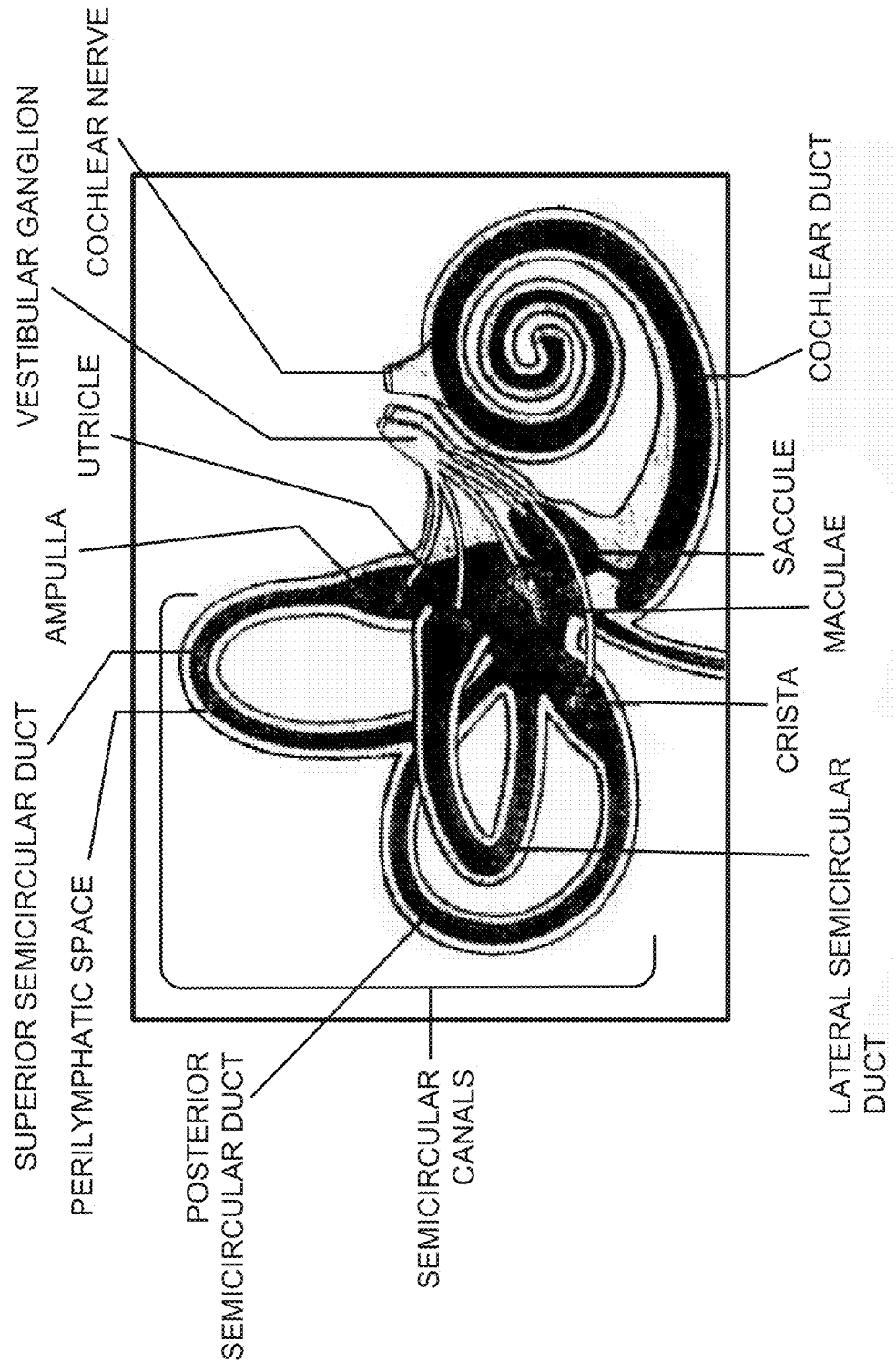
FIG. 5A is a diagram of the inner ear (from *Clinical Neuroanatomy and Related Neuroscience*, Fourth ed., Fitzgerald and Folan, eds., Saunders publishing, 2001).
Figure 5B:
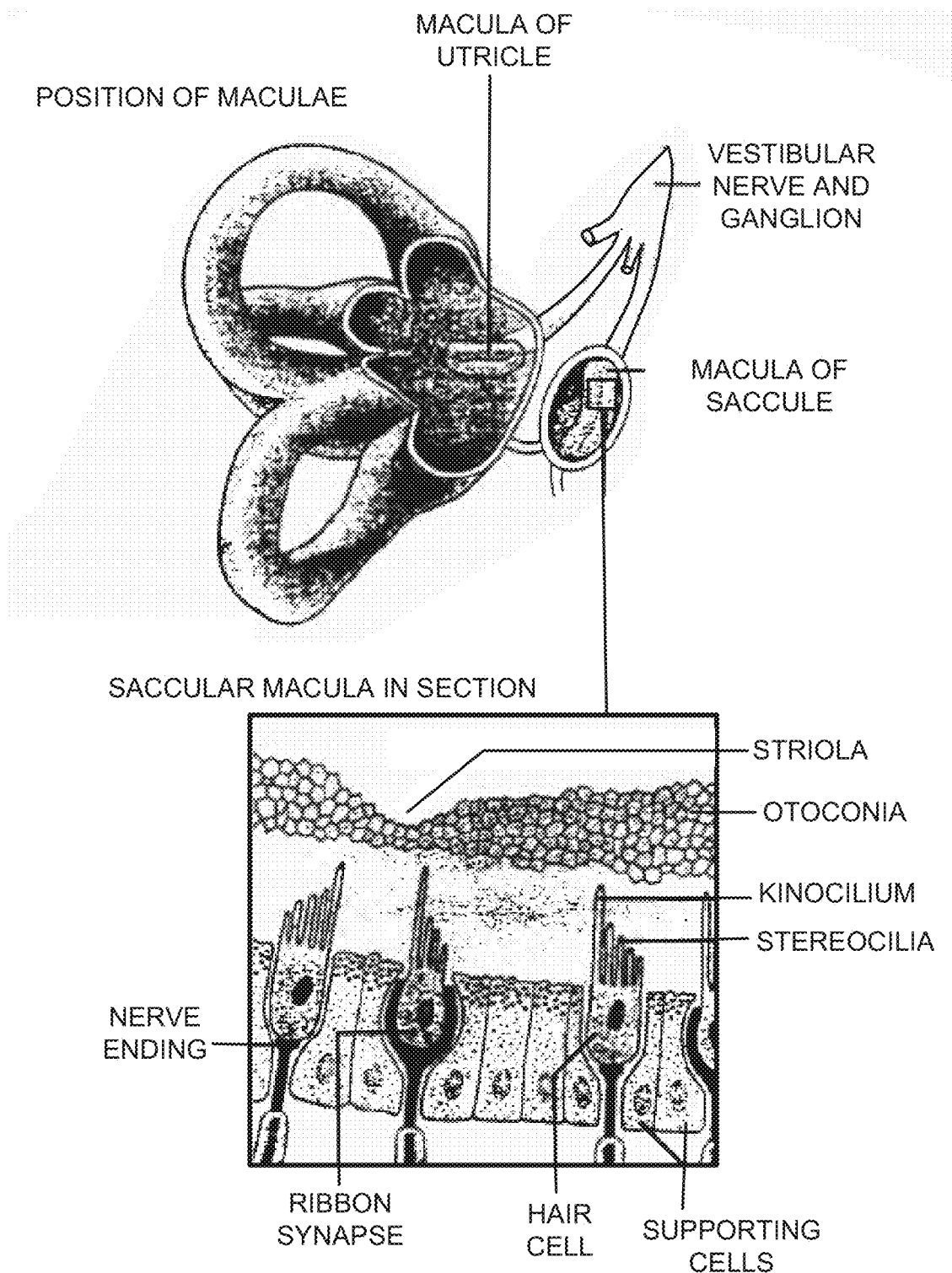
FIG. 5B is a diagram of the semicircular canals and the saccular macula of the inner ear (from *Clinical Neuroanatomy and Related Neuroscience*, Fourth ed., Fitzgerald and Folan, eds., Saunders publishing, 2001).
Figure 5C:
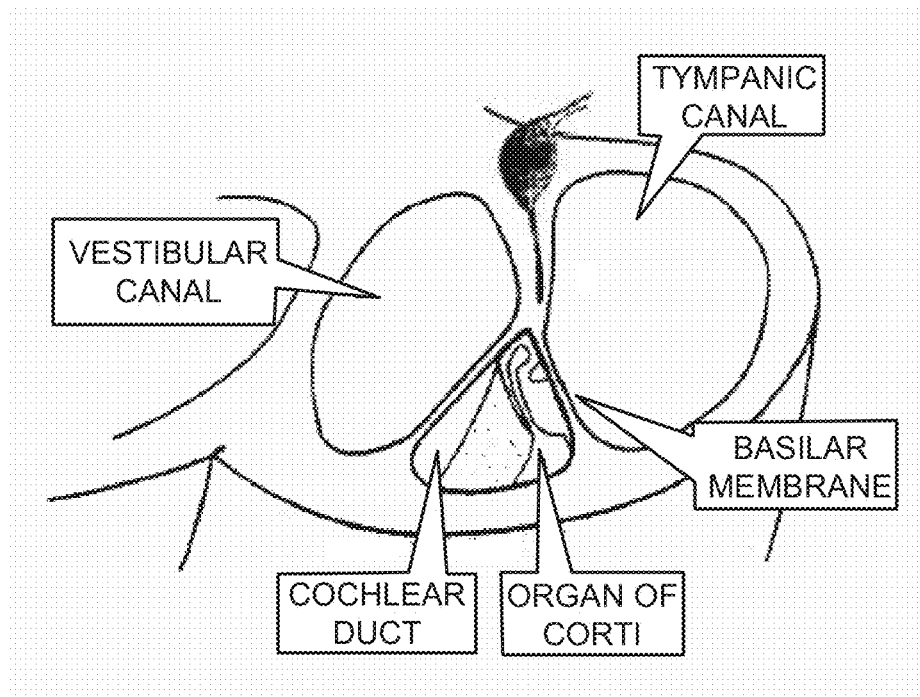
FIG. 5C is a diagram of the cochlea, in section, of the inner ear.

We have developed, inter alia, methods for identifying agents that cause stem cells or progenitor cells to differentiate (fully or partially) into cells of the inner ear. The methods are amenable for use in identifying genes that, when expressed or silenced, can promote or inhibit the differentiation of stem cells into inner ear cells. The methods and agents are useful for treating any disorder that arises as a consequence of cell loss in the ear, such as hearing impairments, deafness, and vestibular disorders.

Stem cells are unspecialized cells capable of extensive proliferation. Stem cells are pluripotent and are believed to have the capacity to differentiate into most cell types in the body (Pedersen, *Scientif. Am.* 280:68, 1999), including neural cells, muscle cells, blood cells, epithelial cells, skin cells, and cells of the inner ear (e.g., hair cells and cells of the spiral ganglion). Stem cells are capable of ongoing proliferation in vitro without differentiating. As they divide, they retain a normal karyotype, and they retain the capacity to differentiate to produce adult cell types. Stem cells can differentiate to varying degrees. For example, stem cells can form cell aggregates called embryoid bodies in hanging drop cultures. The embryoid bodies contain neural progenitor cells that can be selected by their expression of an early marker gene such as Sox1 and the nestin gene, which encodes an intermediate filament protein (Lee et al., *Nat. Biotech.* 18:675-9, 2000).

Stem cells useful for generating cells of the inner ear can be derived from a mammal, such as a human, mouse, rat, pig, sheep, goat, or non-human primate. Furthermore, stem cells can be derived from any number of tissues including, but not limited to, an ear, eye, bone marrow, blood, or skin. For example, stem cells have been identified and isolated from the mouse utricular macula (Li et al., *Nature Medicine* 9:1293-1299, 2003). Stem cells useful for generating cells of the inner ear can be adult stem cells, and therefore derived from differentiated tissue, or the cells can be from embryonic tissue.

The changes that induce a cell to differentiate, such as into a hair cell or a spiral ganglion neuron, involve altered biochemical pathways that lead to a specific phenotype. These alterations are a result of the expression of specific genes, and this expression pattern is influenced by signals from the environment of the cell including cell-cell contact, oxygen content, nutrient availability, ligands that bind to receptors on the cells, temperature, and other factors. Stem cells are adaptive in nature, and their response to changes in these signals triggers the differentiation process.

Proteins that influence (e.g., promote or inhibit differentiation) the phenotype of inner ear cells include developmental regulators, cell cycle inhibitors, transcription factors and other regulatory proteins that act on stem cells. The phenotype of the cell includes the characteristics that distinguish it from other cell types. For example, the phenotype of a hair cell is distinct from the phenotype of a spiral ganglion cell.

Agents capable of causing stem cells to differentiate are referred to as differentiation agents. Differentiation agents can be, for example, small molecules, antibodies, peptides (e.g., peptide aptamers), antisense RNAs, small inhibitory RNAs (siRNA), or ribozymes. Differentiation agents, such as small molecules, can modulate the activity of one or more of the proteins that influence cell phenotype by altering the activity of a growth factor or receptor, an enzyme, a transcription factor, or a cell-specific inhibitor. These molecules can change the binding affinity of a protein for another protein, or can bind in an active site of an enzyme or act as an agonist or antagonist of a ligand binding to a receptor. Some types of differentiation agents, such as small inhibitory RNAs (siRNAs), antisense RNAs, or ribozymes, can modify the expression pattern of genes that encode these proteins. Furthermore, the agents can be useful as therapeutic agents for treating hearing disorders or vestibular dysfunction.

Many different genes are required for the development of the structure and different cell types of the ear. The methods featured in the invention are useful for identifying these genes. The identified genes and gene products can be targets for therapeutic agents and methods for treating hearing disorders and vestibular dysfunction. Indications suited for the methods and therapeutic agents featured in the invention are discussed in greater detail below.

Screening Methods. Screening methods are provided. For example, methods of identifying a differentiation agent that can cause a stem cell to differentiate, at least partially, into a cell of the inner ear or a precursor of the inner ear are features of the invention. A differentiation agent can be a polypeptide, such as an aptamer or antibody; a nucleic acid, such as DNA or RNA; or a compound, such as a small molecule. According to one exemplary method, an agent is contacted with a stem cell, and the stem cell is determined to differentiate, at least partially, into a cell of the inner ear, such as a hair cell or cell of the spiral ganglion. The agent can be naturally occurring or synthetic. The agent can be obtained from a library, or the agent can be a candidate molecule identified by other methods. The candidate agent can have been previously identified as a modulator of a gene or protein known to be active in cells of the inner ear.

A variety of methods can be utilized to determine that a stem cell has differentiated at least partially into a cell of the inner ear. For example, the cell can be examined for the expression of a cell marker gene. Hair cell marker genes include myosin VIIa (myoVIIa), Math1, α9 acetylcholine receptor, espin, parvalbumin 3, and Brn3.1. A pluripotent stem cell does not express these genes. A stem cell that propagates and produces a cell expressing one or more of these genes, has produced a hair cell, i.e., the stem cell has differentiated at least partially into a hair cell. A stem cell that has differentiated into a progenitor cell (a precursor of hair cells) expresses early ear marker genes such as Sox1, Nestin, Pax2, Bmp7, Jagged1, or $p27^{Kip1}$. A progenitor cell can express one or more of these genes. The progenitor cells can be propagated in serum-free medium in the presence of growth factors. Removal of growth factors will induce the cells to differentiate further, such as into hair cells.

Identification of a hair cell or hair cell progenitor (e.g., a hair cell or progenitor cell that differentiated from a stem cell) can be facilitated by the detection of expression of tissue-specific genes. Detection of gene expression can be by immunocytochemistry. Immunocytochemistry techniques involve the staining of cells or tissues using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized. The protein marker can also be detected by flow cytometry using antibodies against these antigens, or by Western blot analysis of cell extracts.

Tissue-specific gene expression can also be assayed by detection of RNA transcribed from the gene. RNA detection methods include reverse transcription coupled to polymerase chain reaction (RT-PCR), Northern blot analysis, and RNAse protection assays.

Identification of a differentiated hair cell or spiral ganglion cell can also be assayed by physiological testing to determine if the cells generate conductance channels characteristic of mature hair or spiral ganglion cells.

In some embodiments, a candidate differentiation agent can be tested against stem cells that have been engineered to express a reporter gene that facilitates detection of cells converted into inner ear cells. These engineered stem cells make up a reporter cell line.

A reporter gene is any gene whose expression may be assayed; such genes include, without limitation, green fluorescent protein (GFP), α-glucuronidase (GUS), luciferase, chloramphenicol transacetylase (CAT), horseradish peroxidase (HRP), alkaline phosphatase, acetylcholinesterase and β-galactosidase. Other optional fluorescent reporter genes include but are not limited to red fluorescent protein (RFP), cyan fluorescent protein (CFP) and blue fluorescent protein (BFP), or any paired combination thereof, provided the paired proteins fluoresce at distinguishable wavelengths.

A reporter gene can be under control of a promoter that is active in cells of the inner ear, including progenitor cells and cells at varying degrees of differentiation, but not in stem cells. Ideally, the promoter is stably upregulated in the differentiated cells or progenitors cells to allow assessment of the partially or fully differentiated phenotype (e.g., expression of the reporter gene and further identification of genes known to be expressed in the inner ear). In one exemplary embodiment, the luciferase gene is the reporter gene, which is under control of a promoter active in hair cells, such as a myoVIIa promoter. Since myoVIIa is primarily expressed in hair cells and in only a few other cell types, the partial or full conversion of the stem cells to hair cells will result in increased luminescent signal, whereas conversion of stem cells to most other cell types will not increase luciferase expression. Other promoters appropriate for use with a reporter gene for identifying differentiated hair cells include myoVIIa, Math1, α9 acetylcholine receptor, espin, parvalbumin 3, and Brn3.1. In some cases it may be necessary to optimize the expression system by performing initial control experiments with various promoters to determine which will work best in the given culture conditions with the particular stem cells (e.g., origin of stem cells) and reporter gene used.

Different types of stem cells can be used for the screening assays, including mouse and human adult stem cells from the ear, bone marrow, or other tissue sources, and embryonic stem cells from mouse or human. Stem cells isolated from other mammalian species are also acceptable for the screening methods described herein.

To determine whether a differentiation agent can induce stem cells to differentiate at least partially into a cell of the spiral ganglion, rather than a hair cell, methods are provided for determining the expression of genes known to be expressed in such cells in vivo. Genes expressed in the spiral ganglion, and useful as cell marker genes, include ephrinB2, ephrinB3, trkB, trkC, GATA3, BF1, FGF10, FGF3, CSP, GFAP, and Islet1.

Secondary assays can be used to confirm, or provide more definitive evidence, that a cell has differentiated into a cell of the inner ear. For example, a gene useful as a marker for identifying a cell of the inner ear can be expressed exclusively in a particular cell type (e.g., exclusively in a hair cell or exclusively in cells of the spiral ganglion), or the cell may also be expressed in a few other cell types (preferably not more than one, two, three, four, or five other cell types). For example, ephrinB1 and ephrinB2 are expressed in spiral ganglion cells, and also in retinal cells. Thus detection of ephrinB1 or ephrinB2 expression is not definitive proof that a stem cell has differentiated into a cell of the spiral ganglion. Secondary assays can be used to confirm that a cell has developed into a cell of the spiral ganglion. Such assays include detection of multiple genes known to be expressed in the suspected cell type. For example, a cell that expresses ephrinB1 and/or ephrinB2, can also be assayed for expression of one or more of GATA3, trkB, trkC, BF1, FGF10, FGF3, CSP, GFAP, and Islet1. A determination that these additional genes are expressed is additional evidence that a stem cell has differentiated into a spiral ganglion cell.

In embodiments where a primary assay includes the use of a reporter gene under control of a tissue-specific promoter, a secondary assay can include detection of the endogenous protein expressed from the endogenous promoter. For example, in a primary screen that assays for expression of luciferase fused to an ephrinB1 promoter in a plasmid, the secondary screen can include an immunocytochemistry assay to detect endogenous ephrinB1 protein, which is expressed from the endogenous ephrinB1 promoter.

Secondary assays also include detection of the absence of gene expression or the absence of proteins that are not typically expressed in hair cells. Such negative markers include the pan-cytokeratin gene, which is not expressed in mature hair cells but is expressed in supporting cells of the inner ear (Li et al., *Nature Medicine* 9:1293-1299, 2003).

The agents identified as being capable of causing stem cells to differentiate into cells of the inner ear can function by activating a gene or protein necessary for differentiation of a stem cell. For example, a differentiation agent can activate or increase expression or activity of a gene of the hedgehog pathway, such as Sonic hedgehog (Shh). Alternatively, an identified agent can function by inhibiting activity of a gene or protein that prevents differentiation of a stem cell into a cell of the inner ear. For example, the agent can inhibit the gene expression or protein activity of hes1, hes5, p19$^{Ink4d}$ or proteins of the Notch family. Many different proteins have been identified as being important for establishing and maintaining the phenotype of the inner ear. These include developmental regulators, cell cycle inhibitors, transcription factors, and other regulatory proteins known to influence the activity of stem cells. It is not necessary that the effect of an agent on a cell be the complete differentiation of the stem cell. A stem cell that is partially differentiated may continue to express some genes that typically inhibit stem cell differentiation (although expression may be weaker). If the agent triggers the cell to differentiate at least partially into a cell of the inner ear, the agent may be useful as a therapeutic agent or as an agent for generating cells having therapeutic value for treatment of hearing disorders by the methods described herein.

Small molecule libraries can be screened against proteins known to be required for preventing the conversion of stem cells to hair cells or spiral ganglion cells. Transcription factors, for example, are required for proper timing of the differentiation of an embryo, and they can prevent the formation of inner ear cells, such as by preventing mitosis Inhibition of these factors in a stem cell can increase the number of cells that will eventually be converted to the inner ear phenotype. Screening for molecules that can interact with such factors will lead to the discovery of agents that have high affinity for the polypeptide factors. Protein/protein interaction assays are known in the art and include co-immunoprecipitation-based assays; binding assays, such as bead-based binding assays; or cell-based assays such as the yeast two-hybrid assay, or a related method.

The ability of the differentiation agents to inhibit or enhance the biological activity of the proteins can be assessed using assays that measure the conversion of the stem cells to inner ear cells. Such assays are described herein and include the detection of inner ear cell-specific markers, or reporter gene assays, wherein expression of a reporter gene indicates conversion of a stem cell to an inner ear cell.

The screens featured in the invention can also be used to identify agents that increase the yield or rate of differentiation of stem cells. Retinoic acid, for example, can induce stem cells to differentiate into a variety of cell types including, but not specific for, hair cells. Agents can be identified that are more specific for inducing differentiation of cells to hair or spiral ganglion cells.

Stem cells that are grown in the presence of supplemental growth factors, and then transferred to growth medium lacking supplemental growth factors will be induced to differentiate into hair cells. Supplemental growth factors are added to the culture medium. They are not required for cell survival, but the type and concentration of the supplementary growth factors can be adjusted to modulate the growth characteristics of the cells (e.g., to stimulate or sensitize the cells to differentiate). Thus a candidate differentiation agent (e.g., a polypeptide, nucleic acid, or small molecule) can be tested for an effect on the differentiation of the stem cell when the cell is transferred to a medium lacking growth factors and contacted with the agent, as compared to the differentiation of a stem cell that is not contacted with a test agent. Alternatively, or additionally, an effect of the agent can be examined in the presence of growth factors, and the concentration of growth factors can be lowered to increase the likelihood of triggering the cells to differentiate. Concentrations of growth factors can range from about 100 ng/mL to about 0.5 ng/mL (e.g., from about 80 ng/mL to about 3 ng/mL, such as about 60 ng/mL, about 50 ng/mL, about 40 ng/mL, about 30 ng/mL, about 20 ng/mL, about 10 ng/mL, or about 5 ng/mL).

Exemplary supplementary growth factors are discussed in detail below, and include, but are not limited to basic fibroblast growth factor (bFGF), insulin-like growth factor (IGF), and epidermal growth factor (EGF).

Screens provided herein include screens to identify genes that can influence development of cells of the inner ear. The identified genes can be targets of the agents discovered by the screens described above. Genes that can influence development of cells of the inner ear can promote differentiation or inhibit differentiation.

To identify genes that promote differentiation, the reporter stem cells described above can be utilized. These cells express a reporter gene, such as luciferase, under control of a cell specific promoter, or promoter fragment. The promoter can be specific for hair cells (e.g., a myoVIIa, Math1, α9 acetylcholine receptor, espin, parvalbumin 3, or Brn3.1 promoter) or auditory neural cells, such as spiral ganglion cells (e.g., an ephrinB2, ephrinB3, trkB, trkC, GATA3, BF1, FGF10, FGF3, CSP, GFAP, or Islet1 promoter), for example.

According to one exemplary screen, such as a library (e.g., a cDNA library) screen, the candidate genes of the library are cloned into plasmids (standard library screening protocols such as those described in Brent et al. (*Current Protocols in Molecular Biology*, New York: John Wiley & Sons Inc, 2003) can be followed). The plasmid used in the library can contain a constitutive promoter, such as a CMV promoter, that drives expression of the candidate gene. The plasmids of the library are introduced into a reporter stem cell line that is cultured in medium containing supplemental growth factors. The transfection of the plasmids into the reporter cell line is performed such that only one plasmid is introduced into any one cell. The cell is examined for an increase in luminescence, by comparison to a reporter cell that has been transfected with a plasmid lacking the candidate gene. An increase in luminescence indicates that the gene promotes the differentiation of the stem cell into a cell of the inner ear. The specific promoter driving expression of the luciferase gene dictates the cell type for which the reporter assay is useful for monitoring differentiation. For example, if the luciferase gene is under control of a hair cell specific promoter, an increase in luminescence indicates that the candidate gene promotes differentiation of hair cells. If the luciferase gene is under control of a spiral ganglion-specific promoter, an increase in luminescence indicates that the candidate gene promotes differentiation of spiral ganglion cells.

The increase in luminescence can be observed while the cells remain cultured in the presence of growth factors, or the cells can be transferred to lower concentrations of growth factors, or to other modified conditions that may sensitize the cells for differentiation. In yet another alternative, the cells can be completely removed from the supplemental growth factors, to compare the luminescence in the presence and absence of the candidate gene.

The screening method can be modified to identify genes that inhibit differentiation. According to one such modified screen, an inhibitory agent, such as a small interfering RNA (siRNA), antisense RNA, ribozyme, antibody, or small molecule, is contacted with a reporter stem cell. The inhibitory agent targets a candidate gene (e.g., an endogenous candidate gene) for down regulation. For example, an siRNA or antisense RNA can block translation of a target RNA, or an antibody or small molecule compound can block the activity of a target protein.

The reporter stem cells are cultured in the presence of growth factors, and they can remain in the presence of growth factors, when the cell is contacted with the inhibitory agent. Alternatively, the cells can be transferred to a lower concentration of growth factors to sensitize the cells for differentiation. In yet another alternative, the cells can be completely removed from the supplemental growth factors, to compare the luminescence in the presence and absence of the candidate gene.

Following contact with the inhibitory agent, the cell is examined for an increase in luminescence, and the signal intensity is compared to a control cell. The control cell can be contacted with an agent that does not target any gene in the cell, or an agent that targets a gene known not to influence (promote or inhibit) differentiation of stem cells into cells of the inner ear, or the control cell may not be contacted with any agent. An increase in luminescence indicates that the gene can inhibit the differentiation of the stem cell into a cell of the inner ear. As described above, the specific promoter driving expression of the luciferase gene dictates the cell type for which the reporter assay is useful for monitoring differentiation. For example, if the luciferase gene is under control of a hair cell specific promoter, an increase in luminescence indicates that the candidate gene inhibits differentiation of hair cells. If the luciferase gene is under control of a spiral ganglion-specific promoter, an increase in luminescence indicates that the candidate gene inhibits differentiation of spiral ganglion cells. The agent can be tested against different reporter cell lines (e.g., lines for testing differentiation of hair cells, and lines for testing differentiation of spiral ganglion cells). Some candidate genes may be found to inhibit differentiation of stem cells to multiple different tissue cell types.

The screens are useful for determining whether a candidate gene can influence stem cell differentiation. Known candidate genes have previously been implicated in ear development or in disorders related to the ear, and many of these genes are listed in Table 1. The screens are also useful for identifying genes not previously recognized as being involved in ear cell differentiation or function. To identify such genes, libraries can be assayed with the described screens. Libraries can be commercially obtained or can be constructed from nucleic acids isolated from specific desired tissues. The libraries can be cDNA libraries constructed from RNA isolated from a mammal, such as a mouse or a human. The RNA can be isolated from a specific tissue of a mammal, such as the brain (e.g., mouse brain or human striatum). The described screens can be modified for high throughput, such as for use in 96-well plates. An agent identified in a screen as being capable of influencing the differentiation of a stem cell into an ear cell can be used to generate ear cells in the laboratory for further research or for treatment of a hearing disorder or other ear-related disorders.

A plasmid can drive overexpression or low-level expression of a candidate gene or inhibitory agent in a reporter stem cell line. In one embodiment, the plasmid can be an adenoviral vector. For example, an adenoviral vector can drive expression of a candidate gene or an inhibitory agent, such as an siRNA, antisense RNA, or ribozyme. The adenoviral vector can drive expression of the candidate gene or inhibitory agent from a promoter, such as a constitutive promoter (e.g., a CMV or human U6 promoter). Libraries, including overexpression or knockdown libraries, are also suitable for use in the methods described herein.

Treatment methods. The agents (e.g., polypeptides, nucleic acids, small molecules, and the like) identified by the screening methods described above can be used to generate cells for therapeutic use. Treatment methods include generating cells of the inner ear (e.g., hair cells or cells of the spiral ganglion) from stem cells for transplantation into an ear of a human in need thereof. Methods of culturing cells of the inner ear include culturing stem cells under conditions that cause the stem cell to differentiate into a cell of the inner ear. Transplantation of the cells into the inner ear of a subject can be useful for restoring or improving the ability of the subject to hear, or for decreasing the symptoms of vestibular dysfunction. Inner ear cells derived from stem cells according to the methods described herein need not be fully differentiated to be therapeutically useful. A partially differentiated cell that improves any symptom of a hearing disorder in a subject is useful for the therapeutic compositions and methods described herein.

Methods of generating cells of the inner ear are provided. Ear cells or ear cell progenitors can be generated from stem cells isolated from a mammal, such as a mouse or human, and the cells can be embryonic stem cells or stem cells derived from mature (e.g., adult) tissue, such as the inner ear, central nervous system, blood, skin, eye or bone marrow. Any of the methods described above for culturing stem cells and inducing differentiation into ear cells (e.g., hair cells or cells of the spiral ganglion) can be used.

Methods of isolating a stem cell or progenitor cell from the inner ear of an animal are also featured in the invention. These methods include providing tissue from the inner ear of the animal, where the tissue includes at least a portion of the utricular maculae. The animal can be a mammal, such as a mouse, rat, pig, rabbit, goat, horse, cow, dog, cat, primate, or human. The isolated tissue can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. In one alternative, both mechanisms of tissue disruption are used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 μm or less, about 70 μm or less, about 60 μm or less, about 50 μm or less, about 40 μm or less, about 30 μm or less, about 35 μm or less, or about 20 μm or less. The cells can be frozen for future use or placed in culture for differentiation.

The separated cells can be placed in individual wells of a culture dish at a low dilution, and cultured to differentiate and into cells of the inner ear, or to differentiate into inner-ear like cells to various stages of the differentiation process. Thus, partially or fully differentiated cells are useful for the methods described herein. The cells can be separated into one cell per well. Formation of spheres (clonal floating colonies) from the isolated cells can be monitored, and the spheres can be amplified by disrupting them (e.g., by physically means) to separate the cells, and the cells can be cultured again to form additional spheres. Further culturing of the cells in the absence of or in lower amounts of growth factors will induce the spheres (and the cells of the spheres) to differentiate further into more highly developed cells of the inner ear.

Appropriate culture medium is described in the art, such as in Li et al. (supra). For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture. In vitro, stem cells often show a distinct proliferation potential for forming spheres. Thus, the identification and isolation of spheres can aid in the process of isolating stem cells from mature tissue for use in making differentiated cells of the inner ear. The growth medium for cultured stem cells can contain one or more or any combination of growth factors, provided that the stem cells do not differentiate. To induce the cells (and the cells of the spheres) to differentiate, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

The cells can be monitored for expression of cell-specific markers. For example, hair cells can be identified by the expression of myoVIIa, Math1, α9 acetylcholine receptor, espin, parvalbumin 3, or Brn3.1. Cells of the spiral ganglion can be identified by the expression of ephrinB2, ephrinB3, trkB, trkC, GATA3, BF1, FGF10, FGF3, CSP, GFAP, and Islet1.

An agent capable of causing differentiation of a stem cell into a cell of the inner ear can be administered directly to the ear of a human requiring such treatment, and the administration of the agent can generate hair cell growth in the ear (e.g., in the inner, middle, and/or outer ear). The number of hair cells in the ear can be increased about 2-, 3-, 4-, 6-, 8-, or 10-fold or more as compared to the number of hair cells before treatment with the agent. This new hair cell growth can effectively restore or establish at least a partial improvement in the subject's ability to hear. For example, administration of an agent can improve hearing loss by about 5, 10, 15, 20, 40, 60, 80, 100% or more.

Pharmaceutical compositions can include one or more ear cell differentiation agents identified as being capable of causing a pluripotent stem cell to differentiate into a cell of the inner ear. The pharmaceutical compositions provided herein can generate hair cell growth in any region of the ear, such as in the inner, middle, and/or outer regions of the ear. For example, a differentiation agent can generate hair cell growth in the cochlea or the vestibular system of the inner ear. Pharmaceutical compositions can also include any of the secondary factors discussed above, including factors to enhance cell engraftment or neurite extension. Exemplary formulations are described in greater detail below. A composition as described herein can be packaged and labeled for use as a treatment for a hearing disorder.

A human having a disorder of the inner ear, or at risk for developing such a disorder, can be treated with inner ear cells (hair cells or spiral ganglion cells) generated from stem cells. In a successful engraftment, at least some transplanted spiral ganglion neurons, for example, will form synaptic contacts with hair cells and with targets in the cochlear nucleus. To improve the ability of the cells to engraft, the stem cells can be modified prior to differentiation. For example, the cells can be engineered to overexpress one or more anti-apoptotic genes in the progenitor or differentiated cells. The Fak tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted organ of Corti (see for example, Mangi et al., *Nat. Med.* 9:1195-201, 2003). Neural progenitor cells overexpressing $\alpha_v\beta_3$ integrin may have an enhanced ability to extend neurites into a tissue explant, as the integrin has been shown to mediate neurite extension from spiral ganglion neurons on laminin substrates (Aletsee et al., *Audiol. Neurootol.* 6:57-65, 2001). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., *J. Comp. Neurol.* 462:90-100, 2003). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al., *NeuroReport* 12:275-279, 2001). A Sonic hedgehog (Shh) polypeptide or polypeptide fragment (e.g., SHH-N), can also be useful as an endogenous factor to enhance neurite extension. Shh is a developmental modulator for the inner ear and a chemoattractant for axons (Charron et al., *Cell* 113:11 23, 2003).

Any human experiencing or at risk for developing a hearing loss is a candidate for the treatment methods described herein. For example, the human can receive a transplant of inner ear hair cells or spiral ganglion cells generated by exposure to a differentiation agent, or the human can be administered an agent identified as being capable of causing a stem cell to differentiate into a cell of the inner ear. A human having or at risk for developing a hearing loss can hear less well than the average human being, or less well than a human before experiencing the hearing loss. For example, hearing can be diminished by at least 5, 10, 30, 50% or more. The human can have sensorineural hearing loss, which results from damage or malfunction of the sensory part (the cochlea) or the neural part (the auditory nerve) of the ear, or conductive hearing loss, which is caused by blockage or damage in the outer and/or middle ear, or the human can have mixed hearing loss, which is caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

The subject can be deaf or have a hearing loss for any reason or as a result of any type of event. For example, a human can be deaf because of a genetic or congenital defect; for example, a human can have been deaf since birth, or can be deaf or hard-of-hearing as a result of a gradual loss of hearing due to a genetic or congenital defect. In another example, a human can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants. A human can have a hearing disorder that results from aging, or the human can have tinnitus (characterized by ringing in the ears).

A human suitable for the therapeutic compositions and methods featured in the invention can include a human having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Following treatment with an agent or inner ear cell or inner ear cell progenitor described herein, the human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain.

The therapeutic compositions and methods featured in the invention can be used prophylactically, such as to prevent hearing loss, deafness, or other auditory disorder associated with loss of inner ear function. For example, a composition containing a differentiation agent can be administered with a second therapeutic, such as a therapeutic that may effect a hearing disorder. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine.

For example, a human undergoing chemotherapy can also be administered a differentiation agent described herein or an agent identified by a method described herein. The chemotherapeutic agent cisplatin, for example, is known to cause hearing loss. Therefore, a composition containing a differentiation agent can be administered with cisplatin therapy to prevent or lessen the severity of the cisplatin side effect. A composition containing a differentiation agent can be administered before, after and/or simultaneously with the second therapeutic agent. The two agents may be administered by different routes of administration.

The compositions and methods featured in the invention are appropriate for the treatment of hearing disorders resulting from sensorineural hair cell loss or auditory neuropathy. Patients suffering from auditory neuropathy experience a loss of cochlear sensory neurons while the hair cells of the inner ear remain intact. Such patients will benefit particularly from treatment that causes cells (stem cells or progenitor cells) to differentiate into spiral ganglion cells, or from administration of spiral ganglion cells into the inner ear. Patients with sensorineural hair cell loss experience the degeneration of cochlear hair cells, which frequently results in the loss of spiral ganglion neurons in regions of hair cell loss. Such patients may also experience loss of supporting cells in the organ of Corti, and degeneration of the limbus, spiral ligament, and stria vascularis in the temporal bone material. These patients can receive treatment with an agent that causes cells to differentiate into hair cells, or a tissue transplant containing hair cells grafted or injected into the inner ear. The patients may additionally benefit from treatment that causes cells to differentiate into spiral ganglion cells, or from administration of spiral ganglion cells into the inner ear.

Formulations and Routes of Administration. Differentiation agents identified by the methods described above can be formulated for administration to a subject diagnosed as having or at risk for developing a hearing loss or vestibular disorder. Pharmaceutical compositions containing a differentiation agent can be formulated in a conventional manner using one or more physiologically acceptable carriers or excipients. For example, a differentiation agent can be formulated for administration by drops into the ear, insufflation (such as into the ear), topical, or oral administration.

In another mode of administration, the differentiation agent can be directly administered in situ to the cochlea of the inner ear, such as via a catheter or pump. A catheter or pump can, for example, direct a differentiation agent into the cochlear luminae or the round window of the ear.

In another route of administration, a differentiation agent can be injected into the ear, such as into the luminae of the cochlea (e.g., the Scala media, Sc vestibulae, and Sc tympani). Injection can be, for example, through the round window of the ear or through the cochlear capsule.

Ear cells generated by the methods described above can be transplanted, such as in the form of a cell suspension, into the ear by injection, such as into the luminae of the cochlea. Injection can be, for example, through the round window of the ear or through the bony capsule surrounding the cochlea.

The cells can be injected through the round window into the auditory nerve trunk in the internal auditory meatus or into the scala tympani.

The nature of the pharmaceutical compositions for administration is dependent on the mode of administration and can readily be determined by one of ordinary skill in the art. The therapeutic compositions feature in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, "Remington's Pharmaceutical Sciences."

The differentiation agents described herein or identified by a method described herein, can be administered directly to the inner ear (e.g., by injection or through surgical placement). Other compositions (e.g., pharmaceutically acceptable compositions containing stem cells, progenitor cells, or auditory cells differentiated by a method described herein) can also be administered directly to the inner ear. The amount of the differentiation agent or the amount of a cell-based composition may be described as a therapeutically effective amount. Where application over a period of time is advisable or desirable, the compositions of the invention can be placed in sustained released formulations or implantable devices (e.g., a pump).

The pharmaceutical compositions can be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compositions can also be formulated as a depot preparation. Such long acting formulations can be administered by implantation (e.g., subcutaneously). Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions formulated for oral administration can take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or *acacia*); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

The compositions may, if desired, be presented in a pack or dispenser device that may contain one or more unit dosage forms containing the active ingredient. The pack may for example comprise metal or plastic foil, such as a blister pack. The dispenser device may include a liquid dropper for administration of a therapeutic agent dropwise into the ear. The pack or dispenser device can be accompanied by instructions for administration.

The efficacy of the treatment methods described herein can be assayed by determining an improvement in the subject's ability to hear, or by an improvement in other symptoms such as balance. Alternatively, efficacy can be assayed by measuring distortion product otoacoustic emissions (DPOAEs) or compound action potential (CAP).

The pharmaceutical compositions and methods described herein can be used independently or in combination with one another. That is, subjects can be administered one or more of the pharmaceutical compositions, for example, pharmaceutical compositions containing a differentiation agent subjected to one or more of the therapeutic methods described herein, or both, in temporally overlapping or non-overlapping regimens. The subject can also be administered a solution or tissue containing the differentiated cells generated from stem cells as described above. One or both of these therapies can be administered in addition to a mechanical device such as a cochlear implant or a hearing aid, which is worn in the outer ear. When therapies overlap temporally, the therapies may generally occur in any order and can be simultaneous or interspersed.

The differentiation agents for use in the methods featured in the invention can be packaged as pharmaceutical compositions and labeled for any use as described herein. For example, the package can be labeled for use to treat a hearing disorder.

Effective Dose. Toxicity and therapeutic efficacy of the compositions disclosed in the invention (e.g., pharmaceutical compositions including the differentiation agents), can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the specific hearing disorder being treated, and for the specific human being treated. For example, the human can have been deaf from birth due to a genetic or environmental event, or a child or adult human can be losing hearing due to environmental factors such as prolonged exposure to loud noises, or a human can be experiencing a hearing loss due to aging. Therefore the human can be any age (e.g., an infant or an elderly person), and formulation and route of administration can be adjusted accordingly. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Kits. A differentiation agent described herein or identified by a method described herein can be provided in a kit, as can cells that have been induced to differentiate (e.g., stem cells or progenitor cells that have differentiated into, for example, hair cells or hair-like cells). The kit can include (a) the agent, such as in a composition that includes the agent, and (b) informational material. The informational material can be descriptive, instructional, marketing or other material that relates to the methods described herein and/or to the use of the agent for the methods described herein. For example, the informational material relates to the use of a differentiation agent to treat a subject who has, or who is at risk for developing, a hearing disorder. The kits can also include paraphernalia for administering a differentiation agent to a cell (in culture or in vivo) and/or for administering a cell to a patient.

In one embodiment, the informational material can include instructions for administering the differentiation agent and/or cell(s) in a suitable manner to treat a human, e.g., in a suitable dose, dosage form, or mode of administration (e.g., a dose, dosage form, or mode of administration described herein). For example, doses, dosage forms, or modes of administration can be by liquid drops into the ear, such as from a dropper bottle, or the composition can be administered directly to the ear such as through a catheter or pump. In another embodiment, the informational material can include instructions to administer the differentiation agent to a suitable subject, e.g., a human, e.g., a human having, or at risk for developing, a hearing disorder. For example, the material can include instructions to administer the agonist to a subject who has experienced a hearing loss due to a traumatic event, or to a subject who has received a separate therapeutic agent that causes hearing loss, such as the antibiotics and chemotherapeutic agents discussed herein.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. In another embodiment, the informational material of the kit is contact information, such as a physical address, email address, website, or telephone number, where a user of the kit can obtain substantive information about the hedgehog pathway agonist and/or its use in the methods described herein. Of course, the informational material can also be provided in any combination of formats.

In addition to the differentiation agent, the composition of the kit can include other ingredients, such as a solvent or buffer, a stabilizer, a preservative, a fragrance or other cosmetic ingredient, and/or a second agent for treating a condition or disorder described herein (e.g., a hearing disorder). Alternatively, the other ingredients can be included in the kit, but in different compositions or containers than the agent. In such embodiments, the kit can include instructions for admixing the agent and the other ingredients, or for using the agent together with the other ingredients.

The differentiation agent (e.g., a hedgehog agonist) can be provided in any form, including a liquid, dried or lyophilized form. The agent is preferably substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the differentiation agent. In some embodiments, the kit contains separate containers, dividers or compartments for the composition and informational material. For example, the composition can be contained in a bottle (e.g., a dropper bottle, such as for administering drops into the ear), vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the hedgehog pathway agonist. For example, the kit can include a plurality of syringes, ampoules, foil packets, or blister packs, each containing a single unit dose of the hedgehog pathway agonist. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper (e.g., ear dropper), swab (e.g., a cotton swab or wooden swab), or any such delivery device). The device can be a dropper for administration to the ear.

Hedgehog Pathway Agonists as Differentiation Agents. Exemplary candidates for use in the treatment methods and pharmaceutical compositions featured in the invention include hedgehog pathway agonists. A hedgehog pathway agonist is a molecule, such as a polypeptide, drug, or nucleic acid that stimulates a hedgehog signaling pathway.

One exemplary hedgehog pathway agonist is a Sonic hedgehog (SHH) polypeptide (SEQ ID NO:1), or fragment of an SHH polypeptide, particularly an N-terminal fragment (FIG. 1). In vivo, SHH undergoes an autoproteolysis event to generate two biochemically distinct products, an 18K amino-terminal fragment, "N," and a 25K carboxy-terminal fragment, "C" (Lee et al., *Science* 266:1528-1537, 1994). In *Drosophila*, cleavage occurs between residues Gly257 and Cys258 (of a conserved Gly-Cys-Phe tripeptide), and the cleavage at this site is conserved in other organisms, including at the site of the corresponding conserved Gly-Cys-Phe tripeptide in mouse and human SHH proteins Cys197 (Porter et al., *Nature* 374:363-366). For example, the cleavage of human SHH occurs between Gly196 and Cys197. The N-terminal cleavage product is referred to as SHH-N. SHH-N polypeptides can perform the signaling functions of SHH, and are suitable for use in the compositions and treatment methods described herein. An SHH-N polypeptide from any species, preferably a mammal, more preferably a human, can be used for the compositions and treatment methods.

A SHH polypeptide (FIG. 1; SEQ ID NO:1) can be any spliced isoform of SHH, or fragment or modified polypeptide thereof. For example, a "modified" polypeptide can be ubiquitinated, phosphorylated, methylated, or conjugated to any natural or synthetic molecule, such as a fluorescent tag or heterologous polypeptide tag. A hedgehog pathway agonist can be a known homolog of Sonic hedgehog, such as an Indian or Desert hedgehog polypeptide, or any spliced isoform, or fragment or modified polypeptide thereof.

A hedgehog pathway agonist can also be a polypeptide having a sequence that is substantially identical to the amino acid sequence of SHH (SEQ ID NO:1). A "substantially identical" gene or polypeptide is similar in sequence to the human Shh cDNA (SEQ ID NO:2; FIG. 2) or amino acid sequence (SEQ ID NO:8; FIG. 1), respectively. A substantially identical nucleic acid sequence is at least 80% identical to SEQ ID NO:2, and a substantially identical amino acid sequence is at least 80% identical to SEQ ID NO:1. For example, a target DNA or RNA sequence can be 80%, 85%, 95%, or 100% identical. A fragment of a target nucleic acid sequence, e.g., a sequence that encodes an exon, can be at least 80% identical to a fragment of SEQ ID NO:2. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence (e.g., when aligning a second sequence to the SHH amino acid sequence of SEQ ID NO:1, having 462 amino acid residues, at least 139, preferably at least 185, more preferably at least 231, even more preferably at least 277, and even more preferably at least 323, 370, or 416 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (*Nucleic Acids Res.* 25:3389-3402, 1997). An SHH polypeptide or polypeptide fragment, such as SHH-N, or substantially identical polypeptide, such as Dhh or Ihh, can have up to about 20 (e.g., up to about 10, 5, or 3) amino acid deletions, additions, or substitutions, such as conservative substitutions, to be useful for the compositions and methods described herein.

In another aspect, a hedgehog agonist can be a polypeptide that is substantially identical to the amino acid sequence of Indian hedgehog (Ihh; see FIG. 3), or Desert hedgehog (Dhh; see FIG. 4). A hedgehog pathway agonist can also be a polypeptide fragment (e.g., an N-terminal peptide fragment) of Ihh or Dhh.

A hedgehog pathway agonist can act on a nucleic acid of a second (or the same) hedgehog pathway agonist. For example, an agonist can increase gene expression of a hedgehog polypeptide, such as by acting as a transcription factor or an enhancer of transcription (e.g., of a Sonic hedgehog gene), or the agonist can stabilize (e.g., protect from degradation) a RNA transcript of a hedgehog pathway agonist. The hedgehog pathway agonist can also (or alternatively) act on a nucleic acid of a gene that is not a hedgehog pathway agonist, but which otherwise influences differentiation of a stem cell or progenitor cell into a cell of the inner ear.

Nucleic acids, such as DNA plasmids, can be used in the methods and compositions described herein, such as for gene therapy. For example, nucleic acids (and nucleic acid vectors) can encode polypeptides that act as hedgehog pathway agonists, such as by any method described herein.

A hedgehog pathway agonist can be a small molecule, such as Hh-Ag1.3. A small molecule is a chemical compound that affects the phenotype of a cell or organism by, for example, modulating the activity of a specific polypeptide or nucleic acid, such as a hedgehog polypeptide or nucleic acid, within a cell. A small molecule can, for example, affect a cell by directly interacting with a polypeptide or by interacting with a molecule that acts upstream or downstream of the biochemical cascade that results in polypeptide expression or activity.

Other members of the hedgehog signaling pathway, besides hedgehog polypeptides themselves (e.g., SHH, Ihh, Dhh), can be used for the treatment methods and compositions described herein. For example, overexpression or modification of a transcription factor that regulates expression of a hedgehog pathway agonist can stimulate hair cell growth. For example, a Gli transcription factor polypeptide (or a nucleic acid expressing a Gli polypeptide) can be administered. Alternatively, a polypeptide, a small molecule, drug, or other modulatory compound that stimulates Gli activity can function as a hedgehog pathway agonist. The Gli family of transcription factors is known to stimulate transcription of Sonic hedgehog in vivo.

In one alternative, the methods and compositions can include an activator of a hedgehog pathway agonist receptor. For example, a polypeptide, small molecule, or other modulatory compound can activate a Patched and/or Smoothened receptor, both of which are recognized by Sonic hedgehog in vivo. In another alternative, cells can be induced to overexpress one or more of the hedgehog pathway agonist receptors, or nucleic acids can be administered (e.g., by gene therapy) and induced to express exogenous receptors. For example, the receptors are expressed on a cell surface to facilitate interaction with a hedgehog polypeptide and activation of a hedgehog signaling pathway that ultimately leads to the development of a hair cell.

In some embodiments, a hedgehog pathway agonist can stimulate endogenous hedgehog proteins. For example, the methods and compositions can include morphogens, growth factors, hormones, and the like, that stimulate hedgehog protein activity (e.g., upregulate gene expression, stimulate protein modification, or otherwise activate protein activity).

In some embodiments, a hedgehog pathway agonist can inhibit an inhibitor of a hedgehog signaling pathway. An inhibitor can be, for example, a polypeptide (such as an antibody), small molecule, or other modulatory compound that binds, sequesters, or otherwise downregulates a component of the hedgehog signaling pathway or inhibits an inhibitor of a hedgehog signaling pathway.

A hedgehog pathway agonist can also be applied to a tissue ex vivo to induce and/or expand the number of hair cells (or hair-like cells) or the hair cell density of the tissue, such as in culture conditions. The resulting tissue can be administered, such as by grafting to the ear (e.g., to the inner ear) of a subject, thereby treating the subject for a hearing disorder.

While not being bound by theory, a hedgehog pathway agonist (e.g., a polypeptide or small molecule agonist) can stimulate hair cell growth by acting on non-hair cells of the ear and instructing these cells to differentiate into hair cells. The hair cells of the mammalian inner ear, for example, are located in the cochlear organ of Corti, as well as in the vestibular sensory epithelia of the saccular macula, the utricular macula, and the cristae of the three semicircular canals. A hedgehog pathway agonist (e.g., a polypeptide or small molecule agonist) can therefore stimulate hair cell growth, for example, by acting on non-hair cells of the cochlear organ of Corti (supporting cells and other cells) and instructing these cells to differentiate into hair cells.

The invention is further illustrated by the following examples, which should not be construed as further limiting.

EXAMPLES

Example 1

Neurons Were Isolated from the Inner Ear of a Pig Fetus for Use in Transplantation Studies We isolated pig fetal spiral ganglion cells from the inner ear after timed pregnancies and placed the cells in culture for periods up to two weeks. Gestational ages of E36, E41, E49, E60 and E63 were compared. Following isolation of whole cochlea, the tissues containing spiral ganglion cells were separated from other tissues and incubated with trypsin- EDTA at 37° C. for 10 minutes. After three washes with PBS plus DNAse, tissues were triturated with three pre-calibrated flame polished Pasteur pipettes with progressively smaller apertures. Cells were resuspended in PBS plus glucose solution at approximately 100×10⁶/ml. The viability of the cells was determined by trypan blue exclusion assay prior to transplantation. Some cells were plated on poly-D lysine coated 12-well culture plate in complete neurobasal medium.

Immunohistochemical staining revealed that the E36 neurons did not express neurofilament but did express neuron specific enolase. At days E49 and later, the neurons expressed neuron specific enolase and neurofilament as well as galactocerebrosidase. The later time points yielded an increased ratio of connective tissue components relative to neurons. The best yield of cells was at E41 and these cells could be stained with all of these markers. This time point was therefore selected for the isolation of cells for transplantation.

Example 2

Embryonic Stem Cell Cultures Were Established and Controlled Differentiation of Different Cell Types was Observed We established cultures of the murine ES cell lines YC5/EYFP, a derivative of the totipotent cell line R1 (Nagy et al., *Proc Natl Acad Sci USA* 90:8424-8, 1993); R1; ROSA26-6; and Sox1-GFP (Aubert et al., *Nat. Biotechnol.* 20:1240-5, 2002). YC5/EYFP cells carry the gene for enhanced yellow fluorescent protein (EYFP) under control of a promoter composed of a cytomegalovirus immediate early enhancer coupled to the β-actin promoter (Hadjantonakis et al., *Mech. Dev.* 76:79-90, 1998). ROSA26-6 cells and their derivatives express the lacZ gene encoding the bacterial beta-galactosidase enzyme (Pirity et al., *Methods Cell Biol.* 57:279-93, 1998). The Sox1-GFP cells express GFP controlled by the promoter for the early neural marker Sox1.

Low passage ES cells are maintained on a feeder layer of mitotically inactivated primary mouse embryonic fibroblasts (Pirity et al., *Methods Cell Biol.* 57:279-93, 1998). Undifferentiated ES cells proliferate actively and form compact clusters of small cells. We initiated in vitro differentiation of ES cells in hanging drop cultures in the absence of embryonic fibroblast feeder cells and of leukemia inhibitory factor, a cytokine that promotes the pluripotency of ES cells. Within two days, cell aggregates of uniform size termed embryoid bodies form in the hanging drops.

Using a published protocol (Lee et al., *Nat. Biotechnol.* 18:675-9, 2000), we were able to select neuronal progenitor cell populations that express the defining marker protein nestin. Nestin-positive progenitors were subjected to in vitro differentiation conditions (see Lee et al., *Nat. Biotechnol.* 18:675-9, 2000) that led to differentiation of astrocytes and neurons.

Figure 6:
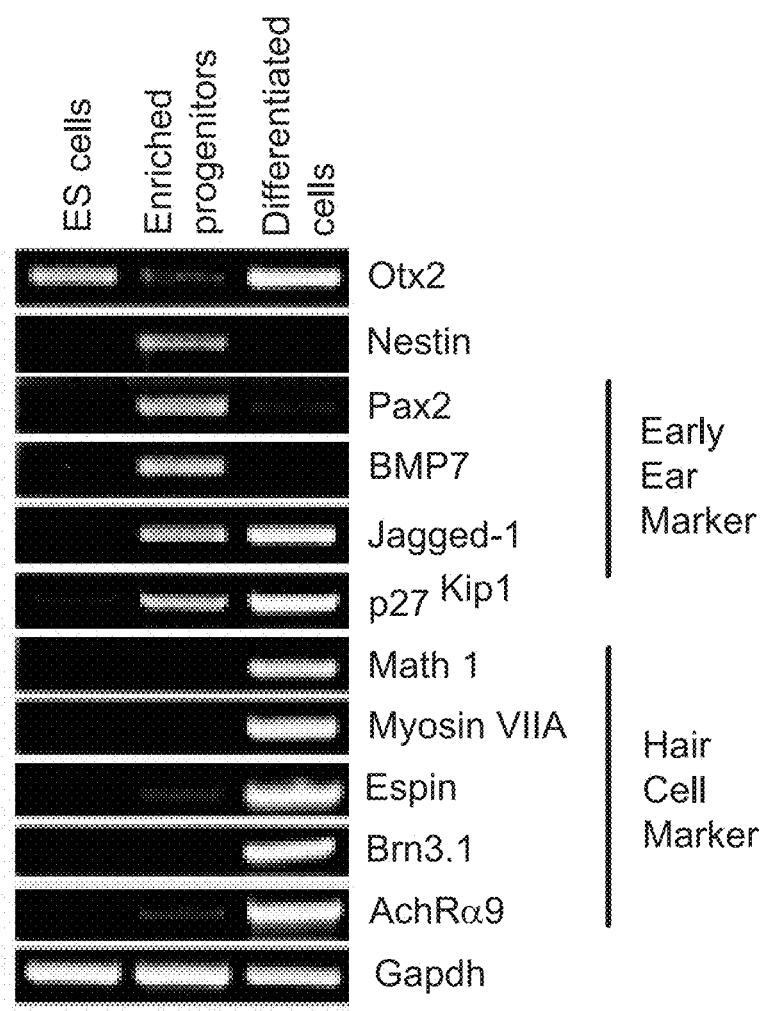
FIG. 6 is a gel indicating the expression of marker genes in embryonic stem (ES) cells, progenitor cells, and differentiated cells. Expression was detected by reverse transcription followed by polymerase chain reaction (RT-PCR), and examination of the amplified products by gel electrophoresis.

Using protocols for the selection of progenitor cells, we were able to select inner ear progenitor cells that express a variety of marker genes indicative of the developing inner ear. In particular, we found after selection from embryoid body-derived cells, cell populations that expressed genes indicative of the otic placode, such as Pax2, BMP4, and BMP7 (Morsli et al., *J. Neurosci.* 18:3327-35, 1998; Groves and Bronner-Fraser, *Development* 127:3489-99, 2000). In addition, we found expression of marker genes for the developing sensory epithelia—for example Math1 (Bermingham et al., *Science* 284:1837-41, 1999), delta1, jagged1 and jagged2 (Lanford et al., *Nat. Genet.* 21:289-92, 1999; Morrison et al., *Mech. Dev.* 84:169-72, 1999). Gene expression was detected by reverse transcription followed by polymerase chain reaction (RT-PCR). The differentiated cells were analyzed 14 days after the removal of bFGF from the culture. The expression of the marker genes correlated with the developmental stage of the progenitor or mature cells as nestin and Pax2 and BMP7 expression decreased upon differentiation of the cells and appearance of hair cell markers (FIG. 6).

Hair cell markers in differentiated cells were also detected by immunohistochemistry. The hair cells produced in this system co-expressed markers important for hair cell differentiation (Math1) and survival (Brn3.1) and markers present in the more fully differentiated cells (myosin VIIa).

In preliminary experiments we explored whether it was feasible to isolate from embryoid bodies clonal lines that represent hair cell and neural progenitors. We were able to generate spheres that contained progenitors, which we identified by expression of the early neural marker Sox1 and the intermediate filament protein nestin. We were able to propagate these progenitor cells in serum-free conditions for more than three months either in form of spheres or as adherent cultures in the presence of mitogenic growth factors. We routinely observed differentiation of the progenitor cells after removal of growth factors in adherent cultures.

Example 3

Different Neuronal Progenitor Cells Were Generated from ES Cells

We explored whether it was feasible to use embryoid bodies to isolate clonal lines that represent neural progenitors. One goal of the project was to generate neurons with different features that could be used to generate neural populations that are very similar to spiral ganglion neurons. The principal idea of this technique was to use the sphere-forming capacity of neural stem cells to clone different cell lines. Our initial results indicated that we were able, for example, to generate spheres that contain neural progenitors, which we identified by expression of the early neural marker Sox1 and the intermediate filament protein nestin.

We were able to propagate these neural progenitor cells in serum-free conditions for more than three months either as spheres or as adherent cultures in the presence of mitogenic growth factors. We routinely observed neural differentiation of the progenitor cells either in aging spheres or after removal of growth factors in adherent cultures. In experiments done with Sox1-GFP ES cells, we were able to generate proliferating neural progenitor lines that expressed nestin and Sox1, visible in real-time by green fluorescence. These cells readily differentiated into morphologically and immunologically distinct neurons after removal of mitogenic growth factors.

We examined the electrophysiological properties of neurons generated from embryonic stem cells and from stem cells harvested from adult ears. Using the strategy outlined above we examined embryonic stem cells differentiated to become presumptive auditory sensory neurons. The cells adopted neuronal morphology and acquired negative resting potentials and the ability to fire action potentials.

Example 4

Development of an Assay for Differentiation of ES Cells

In order to more systematically test the effects of different genes or compounds on the conversion of ES cells to spiral ganglion neurons, we developed a luciferase assay system in which the conversion of the progenitors to the desired cell types is readily detected by a reporter construct. The aim was to have the reporter construct under the control of a promoter that is activated in the differentiated cell but is inactive in the progenitor cells, so that a luciferase signal is generated by differentiation of the cells. The assay can be performed using conditions known to be useful for generating neurons from ES cells. Cells that are grown in the presence of growth factors are cultured in medium without growth factors, and this induces their differentiation to neurons based on the expression of markers. Under these conditions, the reporter cells will differentiate and generate a signal. We used mouse ES cells (ROSA 26) to generate neural progenitors in the presence of EGF, IGF-1 and bFGF. The neural progenitors were used for construction of the reporter cell lines. The progenitor cells were positive for nestin expression and were kept in culture in the presence of bFGF.

To determine whether a cell specific promoter could be measured in this assay, neural progenitors were co-transfected with the firefly luciferase gene controlled by a GFAP promoter and a vector that contains the Renilla luciferase gene under control of a CMV promoter. The firefly luciferase construct was made in the pGL3 basic vector (Promega, Madison, Wis.) that contains the firefly luciferase gene and a multiple cloning site for the promoter. The GFAP promoter inserted into this site allowed us to measure the activity of this promoter relative to the constitutively active control promoter in a separate vector driving the Renilla luciferase. Co-transfection of the vectors into the neural progenitors followed by lysis of the cells and measurement of luciferase activity (using two substrates for measurement of firefly and Renilla luciferase) allowed us to demonstrate that the neural progenitors were initially negative for GFAP expression but after removing bFGF from the culture medium, had increasing amounts of luciferase activity (at 24, 48 and 72 hours). Furthermore, the neural progenitor cells expressed the Renilla and firefly luciferases at levels that were proportional to the amount of vector used for transfection. These results indicate that the assay is useful for determining quantitative effects relating to the differentiation of the cells in response to individual genes or factors.

Example 5

ES Cell-Derived Progenitors Were Grafted into a Developing Chicken Inner Ear

We established microsurgical techniques to manipulate developing chicken ears. For injection of ES cell-derived progenitors, we used beveled glass-capillary micropipettes for injections into the otic pits or vesicles of stage 10-16 chicken embryos (1.5-2.5 days of embryonic development, (Hamburger and Hamilton, *J. Morphol.* 88:49-92, 1951)). Genetically labeled ES cell-derived inner ear progenitors were implanted into the inner ear of chicken embryos and their fate was followed through early otic development. The cells were observed to be engrafted into a preexisting epithelium and certain criteria were identified as being necessary for the cells to engraft. Progenitor cells only survived when implanted as cell aggregates. Progenitor cells that were injected into the otic vesicle in the form of suspensions were not traceable. Integration of cells from the progenitor cell aggregates into the epithelial layers that form the otic vesicle occurred preferentially at sites of epithelial damage. The progenitor-derived cells were incorporated throughout the inner ear, but in our study, we only focused on hair cell development. Murine cells only upregulated hair cell markers when situated in a developing sensory epithelium and only when they were located on the luminal site of the epithelium—in the correct orientation for hair cells. Progenitor-derived cells that we found elsewhere in the inner ear did not display expression of hair cell markers.

In addition to the repopulation of the sensory epithelium (Li et al., *Proc. Natl. Acad. Sci. USA* 100:13495-500, 2003), we also found progenitor cell derivatives outside of the sensory epithelia in the auditory ganglion. In fact, we initially observed more efficient integration of cells into the auditory ganglion than into the cochlear sensory epithelium.

Example 6

An Explant of the Organ of Corti was Established

The organ of Corti from C57BL6 mice at P0-P3 was removed from the cochlea and placed in culture in a collagen matrix or on a collagen coated plate. The morphology of the explants remained intact for up to two weeks. The progenitor cells and differentiated neurons can be tested for their ability to engraft into an explant of the organ of Corti.

Example 7

Transplantation-Repair Studies in the De-afferented Cat

A unilaterally de-afferented cat is a useful animal model for the study of sensorineural hearing loss with either primary neuronal degeneration or primary hair cell damage followed by secondary neuronal degeneration. We cut the auditory nerve in cats and allowed them to survive for up to 1 yr post surgery. Such surgery can result in near complete loss of the auditory nerve, yet all other structures of the cochlea remain normal. Months after nerve section, there appeared to be a reinnervation of the organ of Corti by branches of the facial nerve, which can be seen, in serial sections, streaming through the ganglion without a soma. Within the organ of Corti, this reinnervation appeared as spiraling fibers lining either side of the inner hair cell. These results suggested 1) that hair cells can survive in the adult ear without their afferent innervation, and 2) that the surviving hair cells are likely expressing signals that remain capable of attracting new neuronal contacts.

Figure 7A:
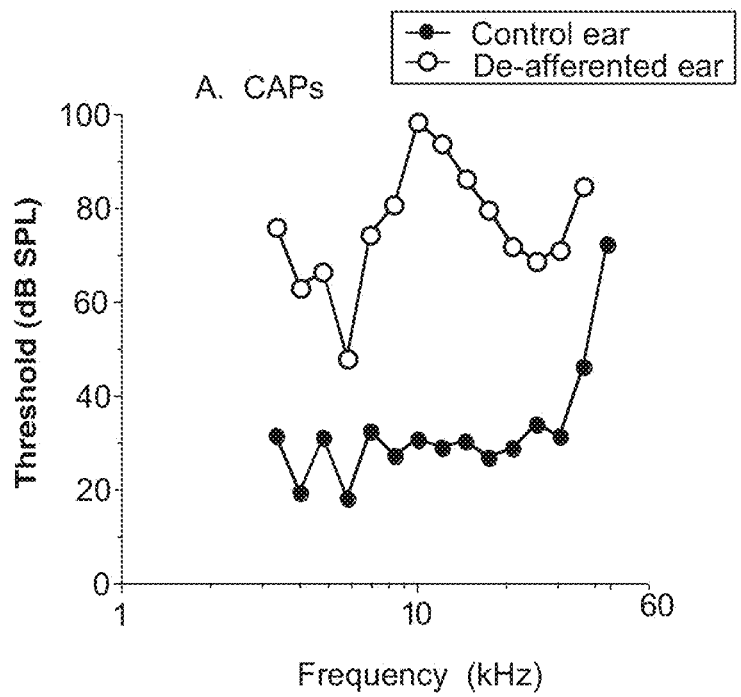
FIG. 7A is a graph illustrating the compound action potential (CAP) threshold elevation in de-afferented and control cat ears. The auditory nerve was cut 10 weeks prior to taking the measurements.
Figure 7B:
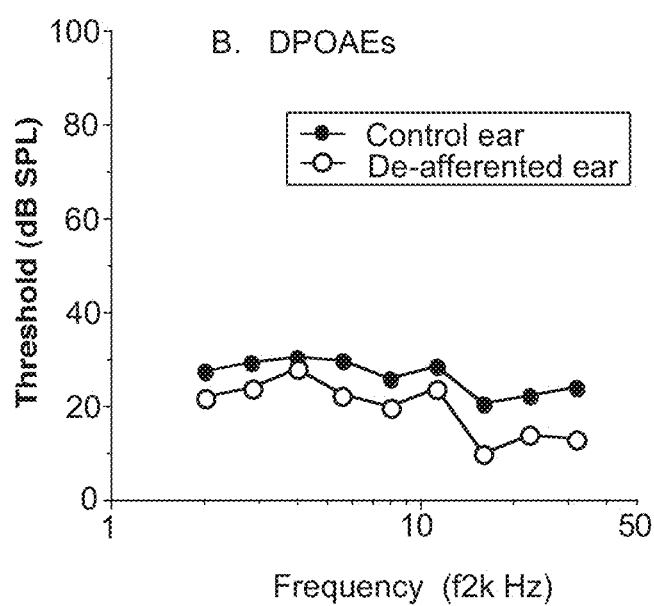
FIG. 7B is a graph illustrating the distortion product otoacoustic emissions (DPOAEs) in the de-afferented and control cat ears. The auditory nerve was cut 10 weeks prior to taking these measurements.

This animal model was used as a platform for neuronal transplantation studies. As shown in FIGS. 7A and 7B, the distortion product otoacoustic emissions (DPOAEs) remained normal in the de-afferented ear, while there was a dramatic elevation of compound action potential (CAP) thresholds in the de-afferented ear. These results indicated that all the processes underlying transduction and amplification in the cochlea were normal in the de-afferented ear. Therefore, this model system is ideally suited to a neuronal transplantation experiment.

We have performed a number of xenotransplantation experiments in the unilaterally de-afferented cat and assessed the extent of incorporation and differentiation of progenitor cells up to 8 weeks post transplantation. The basic approach in the eight animals studied to date has been to 1) cut the auditory nerve bundle near the Schwann glial border, 2) put the animals on cyclosporin immunosuppression therapy, 3) inject neural progenitor cells after a variable recovery interval from 0 to 12 weeks, 4) allow a post-implantation survival of 1-8 weeks, 5) assess functional recovery via a terminal electrophysiological session, and 6) harvest the cochlea and the brain for histological verification of the extent of the primary neural degeneration and the survival and differentiation of transplanted cells.

The progenitor cells injected have included 1) immature spiral ganglion neurons isolated from fetal pigs and 2) mouse ES cells, expressing β-galactosidase reporters. In some cases, the exogenous cells were transplanted into the round window and in other cases into the auditory nerve, just peripheral to the site of the surgical section.

In one study, ES cells were transplanted into the auditory nerve 4 weeks after surgery. When the animal was sacrificed 6 weeks after transplantation, β-galactosidase positive cells were seen only in the vicinity of the electrode track (none were seen anywhere else in the nerve or cochlear nucleus). Some of these cells had neuronal morphology. In one case, a total of 150β-gal positive cells were seen near the electrode track.

Example 8

An Amino-Terminal Polypeptide of Sonic Hedgehog (SHH-N) Stimulates Growth of Hair Cells in Murine Cochlear Explants Explants of the organ of Corti from postnatal day 1 mice were cultured in basic serum-free medium (no growth factor), consisting of serum-free knockout DMEM medium with N2 supplement. Experimental explants were treated with the soluble reagent SHH-N. After 7 days in culture, in situ analysis was performed to examine hair cells through the detection of the hair cell markers myosin VIIA (Myo7a) and Math1. In situ staining revealed that more inner and outer hair cells were present in cultures supplemented with 25 nM SHH-N than in control cultures (N2).

In another experiment, inner ear progenitor cells derived from adult murine inner ear stem cells were cultured in serum-free medium (see Li et al., *Nature Medicine* 9:1293-1299, 2003), and explants were treated with the soluble reagent SHH-N as described above. The number of cells expressing hair cell markers was greater in cultures supplemented with 25 nM SHH-N as compared to control (N2+b27) cultures, and typically the number of cells expressing hair cell markers was about 3-fold greater. Hair cells were identified by in situ staining with an antibody against Myo7a.

Example 9

An Amino-Terminal Polypeptide of Sonic Hedgehog (SHH-N) Stimulates Growth of Hair Cells in Murine Cochlear Explants Chicken otic vesicles were cultured in basic serum-free medium (no growth factor), consisting of serum-free knockout DMEM medium with N2 supplement. Explants were treated with the soluble reagent SHH-N as described above. After 7 days in culture, more hair cells were present in cultures supplemented with 50 nM SHH-N than in control cultures (N2). Hair cell markers were identified by in situ staining with antibodies against myosin VIIA (Myo7a) and hair cell antigen (HCA).

Dosage studies examined the effect of varying concentrations of SHH on hair cell growth in the otic vesicles after three and seven days in culture. After three days in culture, the greatest number of hair cells was observed in cultures containing 12.5 nM SHH-N(FIG. 8A). After seven days in culture, the greatest number of hair cells was observed in cultures containing 50 nM SHH-N(FIG. 8B).

Example 10

Assays to Monitor Differentiation of a Stem Cell into a Hair Cell of the Inner Ear We have developed assays to monitor the differentiation of a pluripotent stem cell into a hair cell of the inner ear. According to one assay, a luciferase gene can be cloned downstream of a myoVIIa promoter. This promoter will activate expression of a reporter gene in any cells that have been converted to hair cells. As an alternative, the Math1 promoter is well characterized and can be used to drive expression of reporter genes in hair cells. Other alternative promoters include the α9 acetylcholine receptor promoter and the espin promoter.

The myoVIIa (or Math1) promoter can be obtained by PCR of mouse genomic DNA. PCR can be performed using primers with specific restriction sites for cloning the DNA into the pGL3-Basic Vector (Promega, Madison, Wis.). The PCR product can be purified by agarose gel electrophoresis, gel purified, and cleaved with restriction enzymes. The pGL3-Basic Vector contains the firefly luciferase gene and a multiple cloning site upstream of the open reading frame. The purified and cleaved PCR product can be cloned into the multiple cloning site in the proper orientation for directing expression of the luciferase gene.

The myoVIIa promoter-luciferase construct can be transformed into bacteria for plasmid amplification, and plasmids purified from the resulting clones can be transfected into derivatives of the mouse stem cell lines ROSA26 or R1. ROSA26 and R1 cell lines are maintained and propagated in medium containing the growth factors EGF (20 ng/mL), IGF-1 (50 ng/mL), and bFGF (10 ng/mL) (Li et al., *Proc. Natl. Acad. Sci. USA* 100:13495-13500). These cells have the characteristics of progenitor cells and have the ability to differentiate into hair cells, but the myoVIIa gene is not activated. A baseline level of luciferase expression can be measured while the cells are in this progenitor state. Removal of the cells to medium lacking growth factors will induce the cells to differentiate into hair cells, which can be detected by an increase in luciferase expression. To detect luminescence, the cells can be lysed and incubated with substrate and the luminescence measured with a device, such as luminescence spectrometer.

Following the initial assay in mouse embryonic stem cells for transfection and conversion of stem cells to hair cells, the assay can be performed in other cell types, such as neural stem cells and bone marrow derived stem cells.

The assay can be performed using a clonal population of cells. To obtain a clonal cell line, cells transfected with myoVIIa-luciferase are selected by growth on G418. The myoVIIa-luciferase reporter cells can be grown in a 10 cm dish until colonies are apparent. The individual colonies can be then be ring-cloned. Alternatively, if the cells are capable of growth at low density, the cells can be grown in 96 well plates at dilutions of up to 1 cell per well, and wells that have apparent cell growth will be harvested. The cells can be propagated to obtain large numbers and can then be subjected to the luciferase assay to determine the effect of candidate genes on the conversion to the hair cell phenotype.

Example 11

Assays to Identify Genes Involved in the Differentiation of Cells of the Inner Ear We have developed assays to identify genes that influence the differentiation of pluripotent stem cells or progenitor cells into hair cells or spiral ganglion cells (or cells that have differentiated to a point sufficient to act as hair cells or spiral ganglion cells; we may refer to these cells herein as "hair-like" cells or "ganglion-like" cells). These genes can have a positive influence, in which case expression of the gene promotes cell differentiation (whether through a positive action or by inhibiting an inhibitor), or a negative influence, in which case expression of the gene inhibits cell differentiation. According to one assay, the myoVIIa-luciferase reporter cells described in Example 10 can be grown in medium containing EGF, IGF-1, and bFGF. The cells can be transfected with a candidate gene (or a biologically active fragment thereof) expressed from a vector such as a plasmid. Expression can be regulated by an inducible promoter or by a constitutively active promoter such as a CMV promoter. Exemplary candidate genes are described in Table 1, and any of the genes or types of genes described in Table 1 can be used in the screening methods of the invention, regardless of the exact manner in which the screen is configured (e.g., regardless of whether the screen is conducted with a single cell; a population of cells; a stem cell or progenitor cell; a pure or impure population of stem cells or progenitor cells; or in culture or in vivo).

TABLE 1

Genes that may influence differentiation of pluripotent stem cells to hair cells or spiral ganglion cells.

| Gene family | Exemplary Candidate Genes |
| --- | --- |
| Basic helix-loop-helix transcription factors | Math1, Brn3.1, Brn3.2, Hes1, Hes5, neurogenin-1, NeuroD |
| Notch Pathway factors | Jagged1, Jagged2, Delta1, Notch1, Lunatic fringe, Numb |
| WNT pathway genes | Wnt7a |
| Cell Cycle regulators | $p27^{Kip1}$ |
| Sonic hedgehog pathway genes | Shh, Bmp4 |
| Growth factors and growth factor receptors | Fgfr3, Fgfr1, Fgfr2, Fgf10, Fgf2, Fgf3 |
| Zinc finger and homeobox transcription factors | GATA3, Pax2 |
| Neurotrophins | Neurotrophin-3, BDNF |

The cDNAs for the candidate genes can be obtained from RNA prepared from various sources include mouse brain or human striatum (Stratagene, La Jolla, Calif.). The RNA can be reverse-transcribed using the Superscript First Strand Synthesis System (Invitrogen, Carlsbad, Calif.) with an oligo(dT) primer and Superscript II reverse transcriptase. The cDNA for each can be cloned into an expression vector containing a hygromycin resistance gene, and transformed into bacterial cells for amplification (pcDNA3.1/hygromycin). The purified vector can be transfected into luciferase expressing cells, such as those described in Example 10, and the cells cultured in medium containing hygromycin. Clonal cell lines can be obtained and expanded in medium containing hygromycin and the growth factor bFGF, EGF, and IGF, as described in Example 10. The expanded cell culture can then be diluted into 96 well plates. The cells can be cultured overnight for initial growth and spreading to take place, and then the cells can be grown in medium without growth factors to induce differentiation. The individual wells can be subjected to the luciferase assay at various times. A method to measure luciferase activity is described above.

As a control experiment, a plasmid expressing a gene that is known to bias the cells to development of a phenotype other than hair cells or spiral ganglion cells can be transfected into luciferase gene-expressing cells. For example, a myoD gene can be transfected into the luciferase-reporter cells to induce differentiation of the cells into muscle cells, or a GFAP gene can be transfected to induce differentiation into ganglion cells.

An alternative assay can be appropriate for identifying genes that inhibit differentiation of stem cells to hair cells. According to this assay, the luciferase reporter stem cells are cultured in low concentrations of growth factors, which will maintain the cells in the precursor state. Small interfering RNAs (siRNAs) that target candidate genes will be introduced into the cells to inhibit the expression of genes whose expression is necessary to maintain the cells in a progenitor state, and thus inhibit the differentiation of the cells into hair cells. Down-regulation of these inhibitory genes will be detected by an increase in luminescence.

To construct the siRNA molecules, short sequences of nucleotides (e.g., sequences of about 21-23 nucleotides) will be selected from the coding sequence of the same group of candidate genes listed above. Synthetic RNAs can be incubated at 90° C. for 1 minute followed by 37° C. for 1 hour to allow the two 21-23 nucleotide strands to anneal. Cationic liposomes can be formed by mixing the siRNAs with oligofectamine (Invitrogen, Carlsbad, Calif.), and this mixture can be used to introduce the siRNA into the luciferase reporter stem cells. Following transfection, the expression of the target gene can be assessed by flow cytometry (for the proteins for which antibodies are available) and by RT-PCR. If a reduction in expression of the targeted protein (or RNA) correlates with an increase in luminescence, it can be concluded that the target gene is an inhibitor of hair cell development. If a decrease in luminescence is detected upon introduction of the siRNA into the cell culture, it can be concluded that the target gene may promote differentiation of stem cells to hair cells. The results of this assay can be compared to the results of the gene overexpression assays described above.

Example 12

Library Screens to Identify Genes Involved in the Differentiation of Stem Cells to Cells of the Inner Ear The inner ear cell development assays described above are amenable to screening large numbers of genes that can be introduced from an expression library.

According to one screening approach, a library can be constructed that includes the luciferase reporter cells described above, transformed with expression vectors containing the test cDNAs. The library can be constructed from inner ear mRNA. The screening assay can be performed in 96-well plates as described above. Detection of luminescence can be performed after various time periods, following the course of differentiation in response to cDNA expression.

In another screening approach, a commercial library of genes cloned into adenoviral vectors can be used to express human genes in the luciferase reporter cell line described above. These assays take advantage of the efficient transduction and long-term expression of the adenoviral delivery system.

Example 13

Purification of Inner Ear Cells Obtained from Stem Cells

The genes identified by the methods described above can be used to induce the differentiation of embryonic stem cells into hair cells or neural cells of the spiral ganglion. These newly generated cells are suitable for transplantation.

Before the cells can be used for transplantation, the differentiated ear cells must be separated from remaining pluripotent cells, and from cells that are otherwise not hair cells or neural cells. To purify the cells, the promoters described above for tissue specific expression in hair cells or spiral ganglion cells can be cloned upstream of a selectable marker, such as the hygromycin resistance gene. Other selectable markers, such as a GFP gene, are appropriate. The methods can be applied to human or mouse embryonic stem cells.

Thus, according to the purification method, a myoVlla promoter can be cloned upstream of a hygromycin resistance gene. The fusion product can be constructed in a plasmid containing a second selectable marker, such as neomycin, under control of a constitutive promoter, such as CMV. Another plasmid can be constructed, wherein a gene identified by the methods of Examples 10-12 is placed under control of a constitutive promoter, such as CMV. The two plasmids can be transfected into a pluripotent human embryonic stem cell. Cells containing the plasmids are selected by growth in medium containing neomycin. Cells that grow in neomycin are expressing the gene of interest, and the neomycin resistance gene. The stem cells are cultured in growth factors such as EGF, IGF-1, and bFGF to maintain the cell in a progenitor state.

To induce differentiation of the cells to form hair cells, the cells containing the engineered plasmid are cultured on hygromycin. The hygromycin media can also include supplemental growth factors. The concentration of growth factors can be reduced to sensitize the cells for differentiation. Some cells may be induced to differentiate by plating on hygromycin in the absence of supplemental growth factors. Cells cultured in hygromycin are newly formed hair cells and can be isolated for use in transplantation.

Other Embodiments

A number of embodiments featured in the invention have been described. Nevertheless, it will be understood that various modifications may be made without departing from the spirit and scope of the invention. Accordingly, other embodiments are within the scope of the following claims.

What is claimed is:

1. A method of treating hearing loss associated with loss of sensory neurons in a human subject, the method comprising:
   providing a therapeutically effective amount of human neural progenitor cells that express nestin and Sox-1; and
   injecting the therapeutically effective amount of neural progenitor cells that express nestin and Sox-1 into the auditory nerve trunk in the internal auditory meatus of the human subject in need thereof, thereby treating the hearing loss in the subject.

2. The method of claim 1, wherein the neural progenitor cells further express at least one marker selected from the group consisting of Pax2, BMP7, Jagged1 and p27kip1.

3. The method of claim 1, wherein the neural progenitor cells further express Pax2.

4. The method of claim 1, wherein the neural progenitor cells further express Pax2, BMP7, Jagged1, and p27kip1.

5. The method of claim 1, further comprising testing the subject for an improvement in hearing.

* * * * *

UNITED STATES PATENT AND TRADEMARK OFFICE
CERTIFICATE OF CORRECTION

PATENT NO. : 9,375,452 B2
APPLICATION NO. : 14/208284
DATED : June 28, 2016
INVENTOR(S) : Albert Edge and Stefan Heller Page 1 of 1

It is certified that error appears in the above-identified patent and that said Letters Patent is hereby corrected as shown below:

In the Specification

Column 1, Line 10, insert -- STATEMENT OF FEDERALLY SPONSORED RESEARCH
This invention was made with government support under Grant No. DC006167 awarded by the National Institutes of Health. The government has certain rights in the invention. --

Signed and Sealed this
Twenty-third Day of May, 2023

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 461
<212> TYPE: PRT
<213> ORGANISM: Homo sapiens

<400> SEQUENCE: 1

```
Met Leu Leu Leu Ala Arg Cys Leu Leu Val Leu Val Ser Ser Leu
 1               5                  10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Gly Arg Tyr Glu Gly Lys
        50                  55                  60

Ile Ser Arg Asn Ser Glu Arg Phe Lys Glu Leu Thr Pro Asn Tyr Asn
65                  70                  75                  80

Pro Asp Ile Ile Phe Lys Asp Glu Glu Asn Thr Gly Ala Asp Arg Leu
                85                  90                  95

Met Thr Gln Arg Cys Lys Asp Lys Leu Asn Ala Leu Ala Ile Ser Val
            100                 105                 110

Met Asn Gln Trp Pro Gly Val Lys Leu Arg Val Thr Glu Gly Trp Asp
        115                 120                 125

Glu Asp Gly His His Ser Glu Glu Ser Leu His Tyr Glu Gly Arg Ala
    130                 135                 140

Val Asp Ile Thr Thr Ser Asp Arg Asp Arg Ser Lys Tyr Gly Met Leu
145                 150                 155                 160

Ala Arg Leu Ala Val Glu Ala Gly Phe Asp Trp Val Tyr Tyr Glu Ser
                165                 170                 175

Lys Ala His Ile His Cys Ser Val Lys Ala Glu Asn Ser Val Ala Ala
            180                 185                 190

Lys Ser Gly Gly Cys Phe Pro Gly Ser Ala Thr Val His Leu Glu Gln
        195                 200                 205

Gly Gly Thr Lys Leu Val Lys Asp Leu Ser Pro Gly Asp Arg Val Leu
    210                 215                 220
```

```
Ala Ala Asp Asp Gln Gly Arg Leu Leu Tyr Ser Asp Phe Leu Thr Phe
225                 230                 235                 240

Leu Asp Arg Asp Asp Gly Ala Lys Lys Val Phe Tyr Val Ile Glu Thr
            245                 250                 255

Arg Glu Pro Arg Glu Arg Leu Leu Leu Thr Ala Ala His Leu Leu Phe
        260                 265                 270

Val Ala Pro His Asn Asp Ser Ala Thr Gly Glu Pro Glu Ala Ser Ser
    275                 280                 285

Gly Ser Gly Pro Pro Ser Gly Gly Ala Leu Gly Pro Arg Ala Leu Phe
    290                 295                 300

Ala Ser Arg Val Arg Pro Gly Gln Arg Val Tyr Val Val Ala Glu Arg
305                 310                 315                 320

Asp Gly Asp Arg Arg Leu Leu Pro Ala Ala Val His Ser Val Thr Leu
                325                 330                 335

Ser Glu Glu Ala Ala Gly Ala Tyr Ala Pro Leu Thr Ala Gln Gly Thr
            340                 345                 350

Ile Leu Ile Asn Arg Val Leu Ala Ser Cys Tyr Ala Val Ile Glu Glu
        355                 360                 365

His Ser Trp Ala His Arg Ala Phe Ala Pro Phe Arg Leu Ala His Ala
    370                 375                 380

Leu Leu Ala Ala Leu Ala Pro Ala Arg Thr Asp Arg Gly Gly Asp Ser
385                 390                 395                 400

Gly Gly Gly Asp Arg Gly Gly Gly Gly Arg Val Ala Leu Thr Ala
                405                 410                 415

Pro Gly Ala Ala Asp Ala Pro Gly Ala Gly Ala Thr Ala Gly Ile His
                420                 425                 430

Trp Tyr Ser Gln Leu Leu Tyr Gln Ile Gly Thr Trp Leu Leu Asp Ser
            435                 440                 445

Glu Ala Leu His Pro Leu Gly Met Ala Val Lys Ser Ser
450                 455                 460

<210> SEQ ID NO 2
<211> LENGTH: 1389
<212> TYPE: DNA
<213> ORGANISM: Homo sapiens

<400> SEQUENCE: 2
atgctgctgc tggcgagatg tctgctgcta gtcctcgtct cctcgctgct ggtatgctcg      60
ggactggcgt gcggaccggg caggggttc gggaagagga ggcaccccaa aaagctgacc      120
cctttagcct acaagcagtt tatccccaat gtggccgaga gaccctagg cgccagcgga      180 aggtatgaag ggaagatctc cagaaactcc gagcgattta ggaactcac ccccaattac      240 aaccccgaca tcatatttaa ggatgaagaa aacaccggag cggacaggct gatgactcag      300
aggtgtaagg acaagttgaa cgctttggcc atctcggtga tgaaccagtg gccaggagtg      360
aaactgcggg tgaccgaggg ctgggacgaa gatggccacc actcagagga gtctctgcac      420
tacgagggcc gcgcagtgga catcaccacg tctgaccgcg accgcagcaa gtacggcatg      480
ctggcccgcc tggcggtgga ggccggcttc gactgggtgt actacgagtc caaggcacat      540
atccactgct cggtgaaagc agagaactcg gtggcggcca atcgggagg ctgcttcccg      600 ggctcggcca cggtgcacct ggagcagggc ggcaccaagc tggtgaagga cctgagcccc      660
ggggaccgcg tgctggcggc ggacgaccag ggccggctgc tctacagcga cttcctcact      720
ttcctggacc gcgacgacgg cgccaagaag gtcttctacg tgatcgagac gcgggagccg      780
```

-continued

```
cgcgagcgcc tgctgctcac cgccgcgcac ctgctctttg tggcgccgca caacgactcg      840
gccaccgggg agcccgaggc gtcctcgggc tcggggccgc cttccggggg cgcactgggg      900
cctcgggcgc tgttcgccag ccgcgtgcgc ccgggccagc gcgtgtacgt ggtggccgag      960
cgtgacgggg accgccggct cctgcccgcc gctgtgcaca gcgtgaccct aagcgaggag     1020
gccgcgggcg cctacgcgcc gctcacggcc cagggcacca ttctcatcaa ccgggtgctg     1080
gcctcgtgct acgcggtcat cgaggagcac agctgggcgc accgggcctt cgcgcccttc     1140
cgcctggcgc acgcgctcct ggctgcactg gcgcccgcgc gcacggaccg cggcggggac     1200
agcggcggcg ggaccgcgg gggcggcggc ggcagagtag ccctaaccgc tccaggtgct     1260
gccgacgctc cgggtgcggg ggccaccgcg ggcatccact ggtactcgca gctgctctac     1320
caaataggca cctggctcct ggacagcgag gccctgcacc cgctgggcat ggcggtcaag     1380
tccagctga                                                            1389
```

<210> SEQ ID NO 3
<211> LENGTH: 411
<212> TYPE: PRT
<213> ORGANISM: Homo sapiens

<400> SEQUENCE: 3

```
Met Ser Pro Ala Arg Leu Arg Pro Arg Leu His Phe Cys Leu Val Leu
  1               5                  10                  15

Leu Leu Leu Leu Val Pro Ala Ala Trp Gly Cys Gly Pro Gly Arg
             20                  25                  30

Val Val Gly Ser Arg Arg Arg Pro Arg Lys Leu Val Pro Leu Ala
         35                  40                  45

Tyr Lys Gln Phe Ser Pro Asn Val Pro Glu Lys Thr Leu Gly Ala Ser
 50                  55                  60

Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Glu Asn
                 85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255
```

Phe Gln Val Ile Glu Thr Gln Asp Pro Pro Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 4
<211> LENGTH: 396
<212> TYPE: PRT
<213> ORGANISM: Homo sapiens

<400> SEQUENCE: 4

Met Ala Leu Leu Thr Asn Leu Leu Pro Leu Cys Cys Leu Ala Leu Leu
 1               5                  10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
    210                 215                 220

-continued

```
Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
            245                 250                 255

Glu Thr Glu Trp Pro Pro Arg Lys Leu Leu Leu Thr Pro Trp His Leu
                260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Leu Gly
385                 390                 395
```